(12) United States Patent
Kano et al.

(10) Patent No.: US 8,021,653 B2
(45) Date of Patent: Sep. 20, 2011

(54) **SHUTTLE VECTOR FOR *BIFIDOBACTERIUM* AND *ESCHERICHIA COLI***

(75) Inventors: Yasunobu Kano, Kyoto (JP); Yoshinori Hamaji, Matsumoto (JP); Minoru Fujimori, Matsumoto (JP); Takayuki Sasaki, Matsumoto (JP); Kyoko Kohno, Kyoto (JP); Jun Amano, Matsumoto (JP); Shun'ichiro Taniguchi, Matsumoto (JP)

(73) Assignee: Anaeropharma Science Inc., Tokyo (JP)

( * ) Notice: Subject to any disclaimer, the term of this patent is extended or adjusted under 35 U.S.C. 154(b) by 924 days.

(21) Appl. No.: 11/718,680

(22) PCT Filed: Nov. 24, 2005

(86) PCT No.: PCT/JP2005/021566
§ 371 (c)(1),
(2), (4) Date: Jun. 25, 2007

(87) PCT Pub. No.: WO2006/057289
PCT Pub. Date: Jun. 1, 2006

(65) Prior Publication Data
US 2010/0129323 A1     May 27, 2010

(30) Foreign Application Priority Data
Nov. 24, 2004   (JP) ................................ 2004-339677

(51) Int. Cl.
*C07H 21/04* (2006.01)
*C12N 15/00* (2006.01)
*C12N 1/21* (2006.01)

(52) U.S. Cl. ................. 424/93.2; 435/320.1; 435/252.3; 536/24.1

(58) Field of Classification Search ........................ None
See application file for complete search history.

(56) References Cited

U.S. PATENT DOCUMENTS

| | | | |
|---|---|---|---|
| 6,080,849 A | 6/2000 | Bermudes et al. | |
| 6,190,657 B1 | 2/2001 | Pawelek et al. | |
| 6,447,784 B1 | 9/2002 | Bermudes et al. | |
| 6,475,782 B1 | 11/2002 | Escobedo et al. | |
| 6,685,935 B1 | 2/2004 | Pawelek et al. | |
| 6,863,894 B2 | 3/2005 | Bermudes et al. | |
| 6,923,972 B2 | 8/2005 | Bermudes et al. | |
| 6,962,696 B1 | 11/2005 | Bermudes et al. | |
| 7,354,592 B2 | 4/2008 | Bermudes et al. | |
| 2002/0054865 A1 | 5/2002 | Fujimori et al. | |
| 2003/0143525 A1* | 7/2003 | Benkovic et al. ................. 435/5 |
| 2004/0219169 A1 | 11/2004 | Bermudes et al. | |
| 2004/0229338 A1 | 11/2004 | King et al. | |
| 2005/0025745 A1 | 2/2005 | Fujimori et al. | |
| 2005/0249706 A1 | 11/2005 | Bermudes et al. | |
| 2007/0009489 A1 | 1/2007 | Bermudes et al. | |

FOREIGN PATENT DOCUMENTS
JP     2002-97144     4/2002

OTHER PUBLICATIONS

Tabata et al. The 245 base-pair oriC sequence of the *E. coli* chromosome directs bidirectional replication at an adjacent region. Nucleic Acids Research, vol. 11, No. 9, pp. 2617-2626, 1983.*
Stalker et al. Nucleotide sequence of the region of an origin of replication of the antibiotic resistance plasmid R6K. Proc. Natl. Acad. Sci. USA, vol. 76, No. 3, pp. 1150-1154, Mar. 1979.*
Sugiura et al. Minimal essential origin of plasmid pSC101 replication: Requirement of a region downstream of iterons. Journal of Bacteriology, vol. 175, No. 18, pp. 5993-6001, Sep. 1993.*
Wickner, SH. Three *Eschrichia coli* heat shock proteins are required for P1 plasmid DNA replication: Formation of an active complex between *E. coli* DnaJ protein and the P1 initiator protein. Proc. Natl. Acad. Sci. USA, vol. 87, pp. 2690-2694, Apr. 1990.*
GenBank Accession No. AB187597.1, GI: 59797008, publicly available Feb. 15, 2005.*
GenBank Accession No. J01749.1, GI: 208958, publicly available Jun. 2002.*
English Translation of the International Preliminary Report on Patentability. Written opinion of the International Searching Authority in corresponding International Application No. PCT/JP2005/021566, Jun. 7, 2007.
Rossi et al., "Improved cloning vectors for *Bifidobacterium* spp.", Ltrs in Applied Microbiology, Feb. 1998, vol. 26, No. 2, pp. 101-104.
U.S. Appl. No. 10/782,899, filed Feb. 23, 2004, Fujimori et al.
U.S. Appl. No. 11/910,880, filed Oct. 5, 2007, Hamaji et al.
Hamaji, et al., "Strong enhancement of recombinant cytosine deaminase activity in *Bifidobacterium longum* for tumor-targeting enzyme/prodrug therapy", Biosci. Biotech. Biochem., Apr. 2007, vol. 71, No. 4, pp. 874-883. Hidaka, et al., "Exogeneous cytosine deaminase gene expression in *Bifidobacterium breve* I-53-8w for tumor-targeting enzyme-prodrug therapy", Biosci. Biotech. Biochem., Dec. 2007, vol. 71, No. 12, pp. 2921-2926.
Park et al., "Sequence Analysis of Plasmid pKJ50 from *Bifidobacterium Longum*," Microbiology, vol. 145, pp. 585-592, 1999.
Tanaka et al., "Structual and Functional Analysis of pTB6 from *Bifidobacterium longum*," Biosci. Biotechnol. Biochem., vol. 69 (2), pp. 422-425, 2005.
International Search Report for application No. PCT/JP2005/021566, completed on Jan. 11, 2006 and mailed on Jan. 17, 2006.
V. Scardovi, in: Bergey's Manual of Systematic Bacteriology. (1986), pp. 1418-1434, vol. 2, eds. Sneath et al., Williams & Wilkins.
T. Mitsuoka, in: The human gastrointestinal tract. In: Wood BJB, ed. The Lactic Acid Bacteria. Essex, UK: Elsevier Science Publishers, 1992; 69-114.

(Continued)

*Primary Examiner* — Jennifer Dunston
(74) *Attorney, Agent, or Firm* — Foley & Lardner LLP

(57) ABSTRACT

The present invention provides a shuttle vector for a microorganism of the genus *Bifidobacterium* (BM) and *Escherichia coli* having a wide host range and a large copy number in BM and capable of highly expressing a desired protein when used as an expression vector; an expression vector capable of expressing a desired gene in BM by use of the shuttle vector; BM transformed with the expression vector; and an antitumor agent comprising the BM as an active ingredient. It comprises a pTB6-derived region portion comprising a replication origin (oriV)-repB region of pTB6 but not comprising MembB, MobA, OrfI, and oriT regions of pTB6 and an *Escherichia coli*-derived plasmid portion comprising a replication origin (Puc Ori) region of *Escherichia coli* but having deleted DNA encoding an N-terminal region of an ampicillin resistance gene (ampR) expression product β-lactamase.

16 Claims, 8 Drawing Sheets

OTHER PUBLICATIONS

H. Yasui and M. Ohwaki. Enhancement of immune response in Peyer's patch cells cultured with *Bifidobacterium breve*. *J. Diary Sci.* 74, 1187-1195 (1991).

B.S. Reddy and A. Rivenson. Inhibitory effect of Bifidobacterium longum on colon, mammary, and liver carcinogenesis induced by 2-amino-3-methylimidazo[4,5-f]quinoline, a food mutagen. *Cancer Res.*, 53, 3914-3918 (1993).

L.C. Duffy, et al. Effectiveness of *Bifidobacterium bifidum* in mediating the clinical course of murine rotavirus diarrhea. *Pediatr. Res.*, 35, 690-695 (1994).

J. M. Saaverdra, et al., Feeding of *Bifidobacterium bifidum* and *Streptococcus thermophilus* to infants in hospital for prevention of diarrhoea and shedding of rotavirus. *The Lancet.* 344, 1046-1049 (1994).

S. A. Ibrahim and A. Bezkorovainy. Inhibition of *Escherichia coli* by Bifidobacteria. *J. Food Prot.* 56, 713-715 (1993).

K. Yazawa, et al., *Bifidobacterium longum* as a delivery system for cancer gene therapy: selective localization and growth in hypoxic tumors. *Cancer Gene Ther.*, 7, 269-274 (2000).

K. Yazawa et al. *Bifidobacterium longum* as a delivery system for gene therapy of chemically induced rat mammary tumors. *Breast Cancer Res. Treat.*, 66, 165-170 (2001).

T. Nakamura, et al. Cloned cytosine deaminase gene expression of *Bifidobacterium longum* and application to enzyme/pro-drug therapy of hypoxic solid tumors. *Biosci. Biotechnol. Biochem.*, 66, 2362-2366 (2002).

M. Fujimori, et al., The genus *Bifidobacterium* for cancer gene therapy. *Curr. Opin. Drug Discov. Devel.*, 5, 200-203 (2002).

H. Matsumura, et al. Construction of *Escherichia coli-Bifidobacterium longum* shuttle vector transforming *B. longum* 105-A and 108-A. *Biosci. Biotechnol. Biochem.*, 61, 1211-1212 (1997).

Minoru, F., et al. Japanese Laid-Open Patent Application No. JP 2002-97144. English Translation of the abstract.

\* cited by examiner

[Fig. 1]
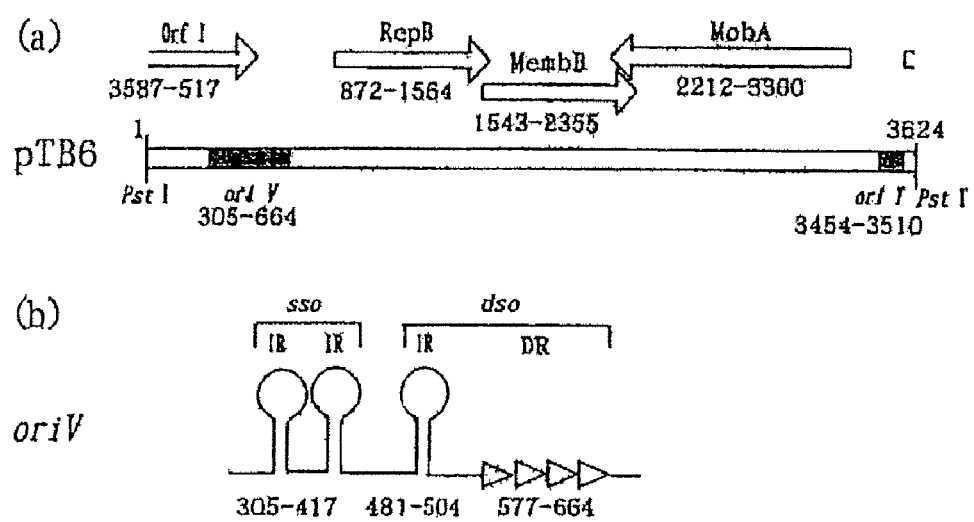

(a)

|  | region 1 | region 2 |
|---|---|---|
|  | 117    138 | 183  188 |
| pTB6 | --FCRLLGVPPSAITQTRYLNQKVLQPIQEECGP--34--VEARKTDGDGKGHWTS--- |
| pKJ36, pB44 | --FCRLLGVSDSTAKSTANLNRVVLKTIAEECGP--34--VEARKTDGDGKGHWTS--- |
| pDOJH10L | --FCRLLSVPKSTAEQVRDLNKRVLKPIIEECGP--34--VEARKAE DA GHWTS--- |
| pNAC2 |  |
| pBL01 | --FCRLLNVSKSTSDSVSNLNRVVLKPIVEECGP--34--VKA KEEQDS GHWTS--- |

(b)

| | nuc position | DR in dso | Number of repeat |
|---|---|---|---|
| pTB6 | 577-664 | AACCTACACCAAAGGGGAGCG | 4 |
| pKJ36, pB44 | 583-670 | ACTTAGTACAAAAGGGAGCGA | 4 |
| pNAC2 | 382-295 |  | 4 |
| pDOJH10L | 8088-8175 | GGGGACAAAAGGGAGCGAACC | 4 |
| pBL01 | 663-750 | TGAGTACAAAATAGGAGCGA/GAT/C | 4 |

(c)

| | nuc position | IR in dso |
|---|---|---|
| pTB6 | 481-504 | AAAAAGGCGCTGTGCGCCCTTTTT |
| pKJ36, pB44 | 487-510 |  |
| pNAC2 | 482-459 |  |
| pDOJH10L | 7988-8011 | AAAAAGGCGCCGTGCGCCCTTTTT |
| pBL01 | 565-588 | AAAAAGGCGCTTTGCGCCCTTTTA |

```
                   Motif I                          Motif III
           1      *27              121      *    *  *   145
pTB6       MAIYHLSVSNVSRASGSR-ATATLSYIT-----TYAIHEDREGNNPHAHILVANRQID
RSF1010    MAIYHLTAKTGSR-SGGQSARAKADYIQ-----TLAIHAGG-GENPHCHLMISERIND
           1       27              108                          131
```

(b)

```
pTB6       CCGGAGGGCGCGCTTACGGAAAATGCAACCTCCGGTTGCATGTAAGTGCGCCCTAAT
           3454                                                3510
                          3169
RSF1010    CCAGTTTCTCGAAGAGAAACCGGTAAGTGCGCCCTCCC
                                                3132
```

[Fig. 3]

[Fig. 4]
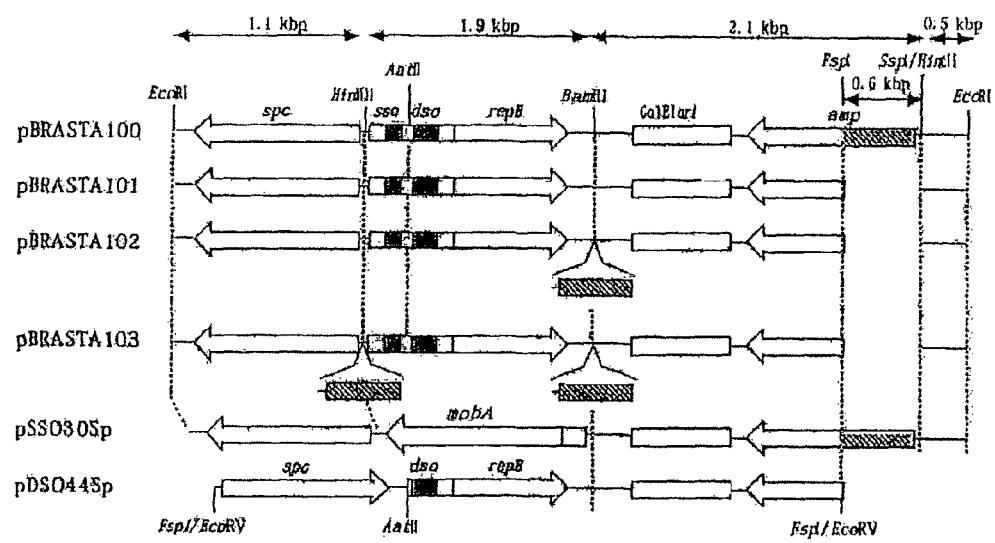

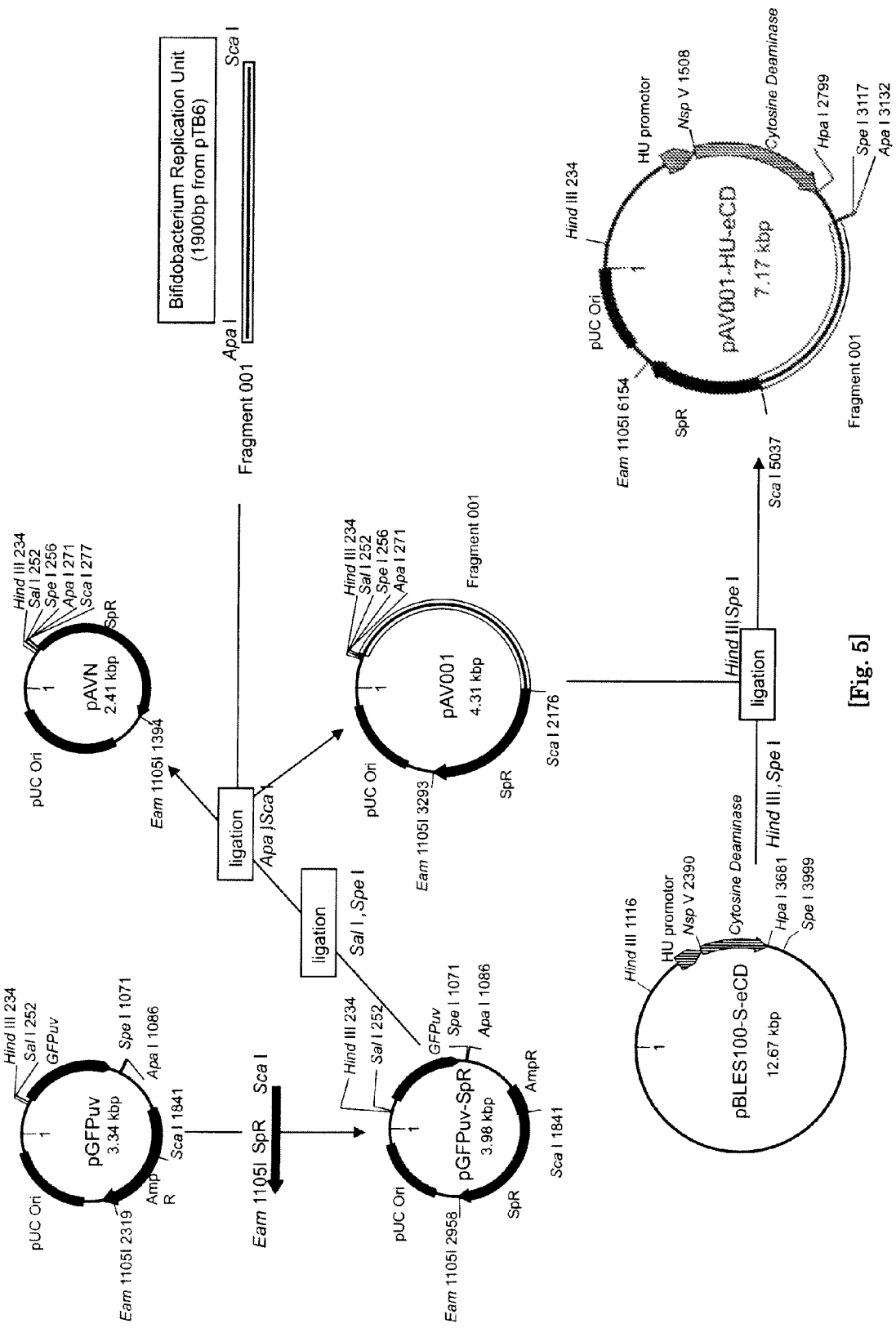
[Fig. 5]

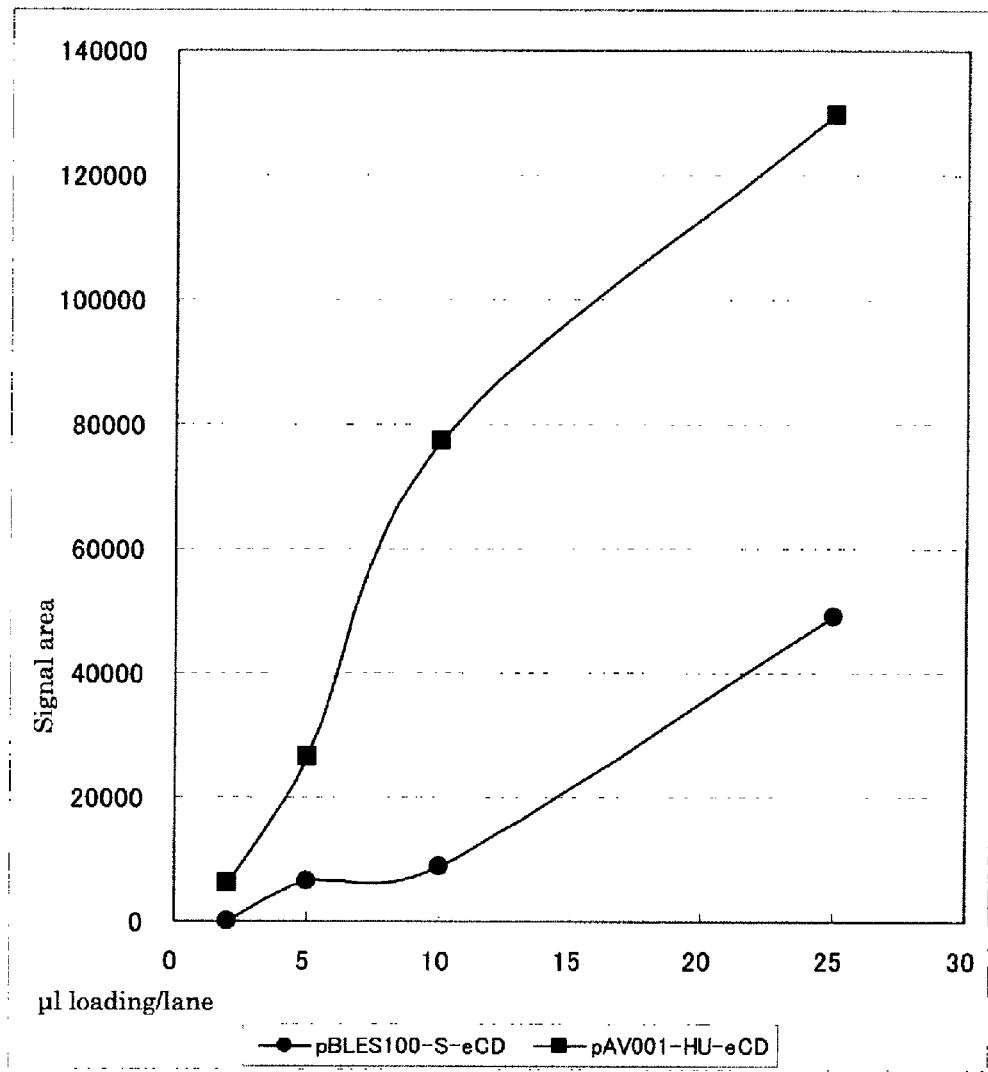
[Fig. 6]

[Fig. 7]
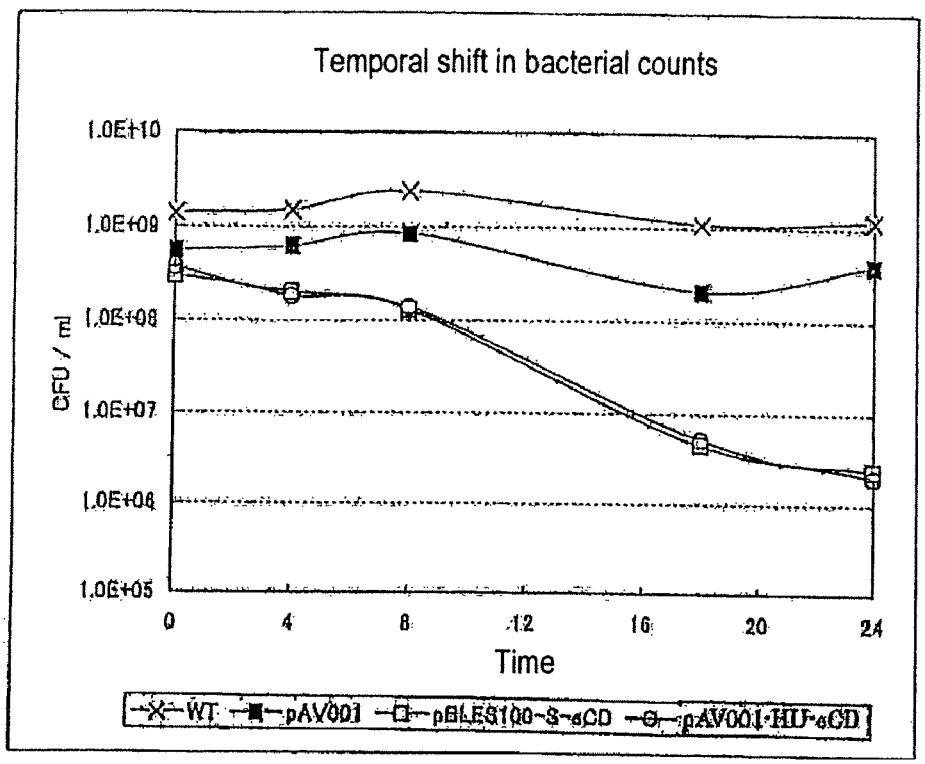
[Fig. 8]
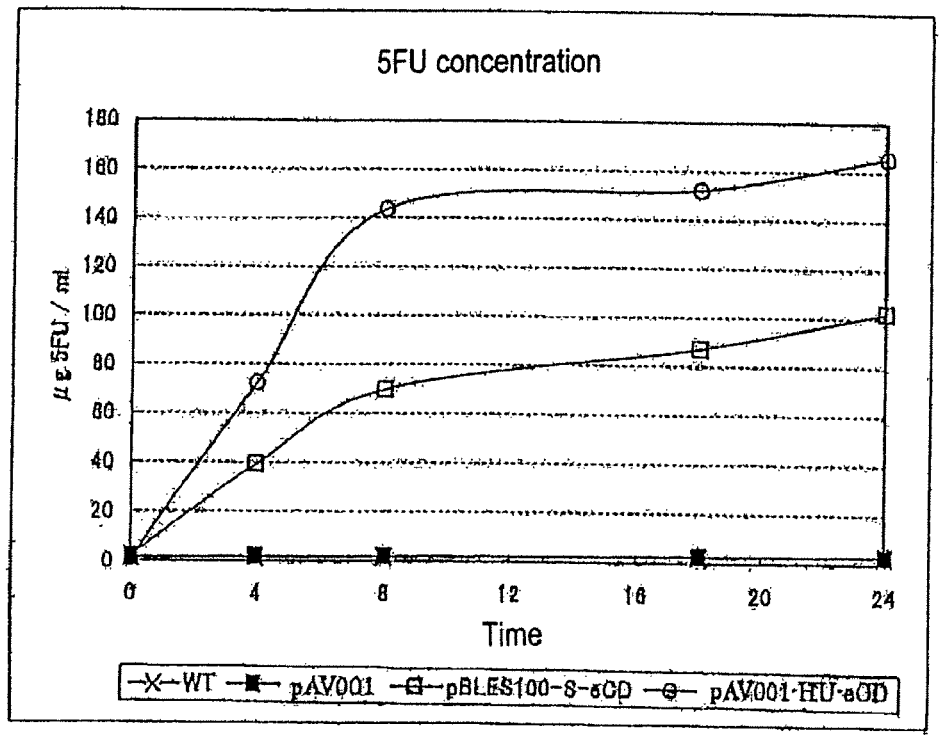

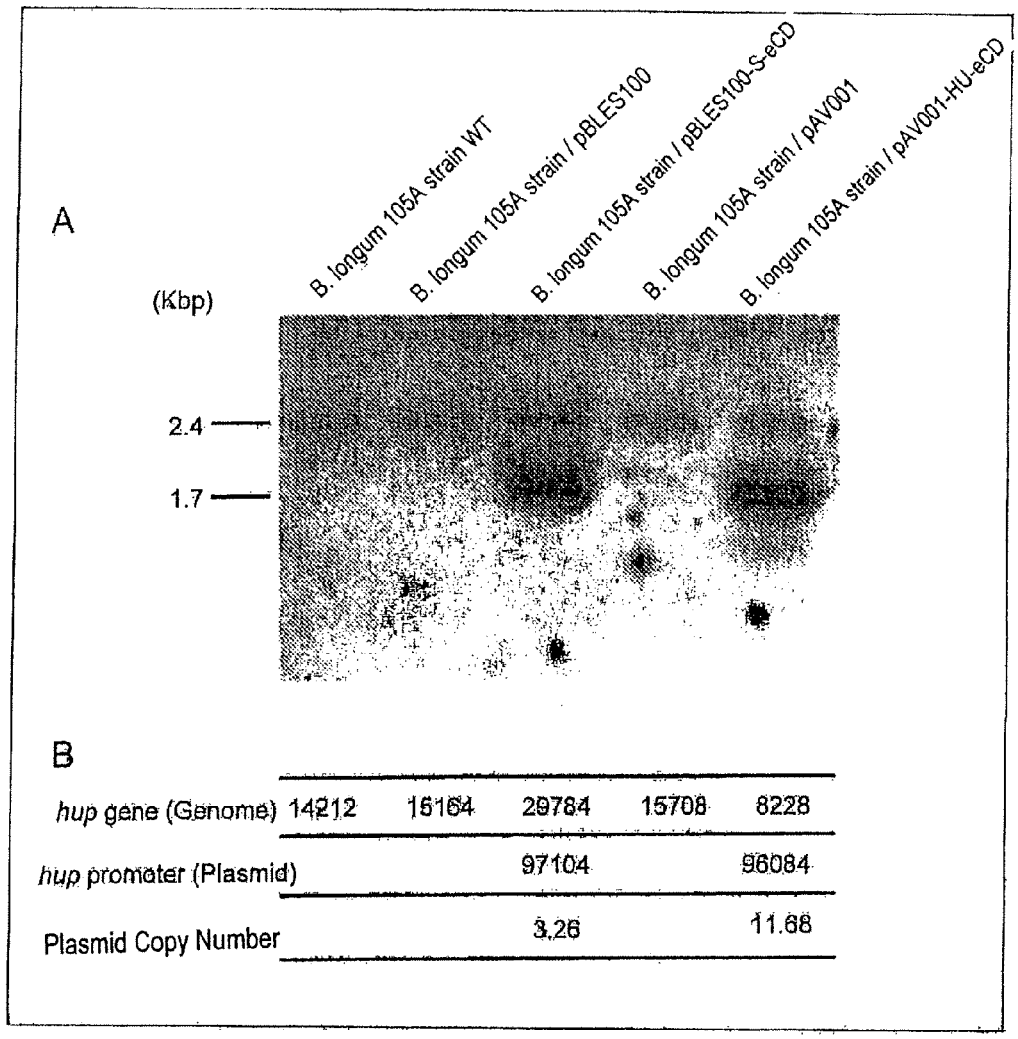
[Fig. 9]

SEQUENCE LISTING

<160> NUMBER OF SEQ ID NOS: 31

<210> SEQ ID NO 1
<211> LENGTH: 3624
<212> TYPE: DNA
<213> ORGANISM: Bifidobacterium longum

<400> SEQUENCE: 1

```
gataggcagg ccagctcaag gcccgcgaga acgacctcgt ggcgcggcgc agggaacgcg    60
aacgcaaggc ccgcaccaag cgcctgatcg aggtcggcgc gatggccgag tcggccgcgg   120
gcttcgaggg aggcgacgag agggccaagg agcacatcgc ccgcctcgtg cagctcggct   180
ccctggtgga gtccctgtgc tccaccgacg tgatggccaa ctacacgagc cgcgaggacc   240
tcagggccac cgtcgccaag gctctggaac acaacgtcag gaccagcgat ggcatgaact   300
ggaacctcca ggacctcgtc tacgaggcgc tgagcgagga atgcgcaaa agggacggcg    360 agatcagcga cccatgggcc aacgacgagg cggacggata ccagccgccc tcatacgagc   420
cggtcaaccc cgaacgcagg actccccaga cgccctccga tggcctgatc tgacgtccga   480
aaaaaggcgc tgtgcgccct ttttaaatct tttataaatc tttttacatt cttttagccc   540
ctccgcagcc ttactctccc aacgggtttc agccgaaacc tacaccaaaa ggggagcgaa   600
cctacaccaa aaggggagcg aacctacacc aaaagggag cgaacctaca ccaaaagggg   660
agctatatac accttttgtt atttaaggtg caagttgtgc tatgctgagg ccatgtccaa   720
tgagatcgtg aagttcagca accagttcaa caacgtcgcg ctgaagaagt cgacgccgt    780 gcacctggac gtgctcatgg cgatcgcctc aagggtgagg gagaagggca cggccacggt   840
ggagttctcg ttcgaggagc tgcgcggcct catgcgattg aggaagaacc tgaccaacaa   900
gcagctggcc gacaagatcg tgcagacgaa cgcgcgcctg ctggcgctga actacatgtt   960
cgaggattcg ggcaagatca tccagttcgc gctgttcacg aagttcgtca ccgacccgca  1020
ggaggcgact ctcgcggttg gggtcaacga ggagttcgcg ttcctgctca acgacctgac  1080
cagccagttc acgcgcttcg agctggccga gttcgccgac ctcaagagca agtacgccaa  1140
ggagttctac cgcaggccca agcagtaccg cagctccgga atctggaaga tcggccgcga  1200
cgagttctgc cgactgcttg gcgttccacc gtcggcaata acccagacac gatatctgaa  1260
tcagaaggtt cttcagccaa ttcaggagga gtgtgggcct ctccttggcc tgaagatcga  1320
gcgccagtac gtgaaacgca ggctgtcggg cttcgtgttc acattcgccc gcgagacccc  1380
tccggtgatc gacgccaggc ccgtggaggc gaggaagacg gacggcgacg gcaagggcca  1440
ttggacgagc gttgccgggt acggcgaggt gttcacgacc acggcgttgt tcgacgtgac  1500
```

-continued

```
ggccgcccgg gctcacttcg acggcaccgt ggaggccggg gaatgccgtt tctcgcgcgt    1560
ttgacgcgcg caaccgcgaa catcatgcgc ggaacgccgg aaggctgttc tagcggccgt    1620
gtccgcgcct ctggggcggg tttgcgcctg ccatgggtcg atctgccgct gttcggcctc    1680
acgctggtct gtgcgctgcc tgatctccct gagcaggtcg gccttggtcc tgggggcgct    1740
tcgctcctcg aacgggccgc tctccccag gtcctcgggc tcgctcaggt ccaacggctc     1800
gtcaccggac ggctcgggcc ggttctctcc ctgtgccggg ttctccgcct gtgcgcgttg    1860
ttctggccat gcgcagtgcg agggccttca cctgttcggg gcttggcttc tcgttctcgg    1920
cccgctcggc cctgttcgag ccgcctctcc agttcggcca cgagcccggt ccttggctgc    1980
atgtcgtggt cgtggatggt cttggtggtc ctcatgcgga acctgttggc ctggtcccag    2040
tcgctcggga tgtcggcgtc ttcgagccat ggcaccgccc cgcgcagctt ctcggactgc    2100
tccccggcca cctgttcggc gttccgcagc agcctgccgc gcttgaagac gttcgcgtcc    2160
ctggcctcgc gcgaggcggc tcgcgccacg tcgatgatct gcttggcggc ctcaaactcc    2220
tcggtgccgt ggctcctcca ccactcctcg cggttcctca cgtcggcctt ggctcccatg    2280
agttttccac ggatcgctgc cgtgtggtcg gccctgtcgg cttcgagctg gcggcgcgcg    2340
tcgccctcga agtagcgcca gttcggctcc ctggccggtt ccggcctcgc ctggcgttgg    2400
cgcagctgcc ctgatcttgg cggcgaacag ctcgcccagg cggtcgaata tccgccgag    2460 ttcggtgcgg atggaggtca gcaggccgtt gctgcgcctg atctcacggt tggcctcgca    2520
cctctcgctg acgcccccgg cccgttcgat ggccctggcc gcgtagccct cgtggatggt    2580
gggttcgagg tcgctgccct ggtcctcgag gctcctgtgg tcgattctcg cggtctcgtc    2640
cagccgcgcg ttacaggtct tcgcccagga ttcgcgcagg gccttgagct tggccttccg    2700
gtcgagcggg ttcagggaca cgctcgtgcg cttccactgc ctgcggcccc gcttgtcggt    2760
cttctgcctg ccggtctcgg ggtcgatcag cggcacccgc tctccccgct cgtccagcac    2820
gtactccatg cgctgcttga gcctggccca gccgcccgtg gccgggtcga tctgccggtt    2880
ggcgacgagg atgtgcgcgt gcggattgtt gccctccctg tcctcgtgga tggcgtaggt    2940
ggccgcgtag ccgtccgcgt tcaggttctc gcggatgtac tcctccagcg cctgcacgcg    3000
ctgcctgggg gtgaactcgc gcggcagggc caccacgatc ttcttggccg gcctcgccgt    3060
ccgtccggtc tcgtgcagct cgaccgcgtt gaacagcacg gcggggtcgg cgaactcggc    3120
cggcgcgccc tccggcagca gggtgccgac gcgcagcacg cgctccttgc gcccgtagtc    3180
gtaggtctcg ccgcgccgct cgtcatgcac ccgcttgccg gtgatgtacg agagcgtggc    3240
cgtggccctg gaaccgctcg cgcggctcac gttggagacg gacagatggt agatcgccat    3300
cggcttcggc tcctttcgtg atcggccagg gcggtggggt gcggggcggc ggccctgcgg    3360 caagggttc ctaggggtgc ggcgagcacc cgctgggcct gccgggaggc tccccggaa     3420 gggtgggaat ccaaagggca aggcccgtgg ccccggagg gcgcgcttac ggaaaatgca    3480
acctccggtt gcatgtaagt gcgccctaat ctttgattag ggatttcctt gctggtagaa    3540
tcatatcacc atacggatga tgcagaccat gtaaggagcc gtttcgatgg tgaagagcct    3600
ggatgagcag atcaagtccc tgca                                          3624
```

<210> SEQ ID NO 2
<211> LENGTH: 600
<212> TYPE: DNA
<213> ORGANISM: Bifidobacterium longum

<400> SEQUENCE: 2

-continued

```
gctgggcgcg gcggccatga agtggcttga caagcataat cttgtctgat tcgtctattt    60
tcaataccct cggggaaata gatgtgaaaa cccttataaa acgcgggttt tcgcagaaac   120
atgcgctagt atcattgatg acaacatgga ctaagcaaaa gtgcttgtcc cctgacccaa   180
gaaggatgct ttatggcata caacaagtct gacctcgttt cgaagatcgc ccagaagtcc   240
aacctgacca aggctcaggc cgaggctgct gttaacgcct tccaggatgt gttcgtcgag   300
gctatgaagt ccggcgaagg cctgaagctc accggcctgt tctccgctga gcgcgtcaag   360
cgcccggctc gcaccggccg caacccgcgc actggcgagc agattgacat tccggcttcc   420
tacggcgttc gtatctccgc tggctccctg ctgaagaagg ccgtcaccga gtgaccttct   480
gctcgtagcg attacttcga gcattactga cgacaaagac cccgaccgag atggtcgggg   540 tcttttttgtt gtggtgctgt gacgtgttgt ccaaccgtat tattccggac tagttcagcg   600
```

<210> SEQ ID NO 3
<211> LENGTH: 35
<212> TYPE: DNA
<213> ORGANISM: Artificial sequence
<220> FEATURE:
<223> OTHER INFORMATION: primer

<400> SEQUENCE: 3

```
ggccggaatt ctgagcaaaa ggccagcaaa aggcc                               35
```

<210> SEQ ID NO 4
<211> LENGTH: 40
<212> TYPE: DNA
<213> ORGANISM: Artificial Sequence
<220> FEATURE:
<223> OTHER INFORMATION: primer

<400> SEQUENCE: 4

```
ggccggaatt cagtactcat atatacttta gattgattta                          40
```

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5

```
gcggcggatc cattgaaaaa ggaagagtat                                     30
```

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6

```
cggccggatc ctgcgcaacg ttgttgccat                                     30
```

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7

```
gcggcaagct tattgaaaaa ggaagagtat                                     30
```

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
cggccaagct ttgcgcaacg ttgttgccat 30

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
aacctacacc aaaaggggag cg 22

<210> SEQ ID NO 10
<211> LENGTH: 13
<212> TYPE: DNA
<213> ORGANISM: Artificial Sequence
<220> FEATURE:
<223> OTHER INFORMATION: primer

<400> SEQUENCE: 10
gtaagtgcgc cct 13

<210> SEQ ID NO 11
<211> LENGTH: 32
<212> TYPE: PRT
<213> ORGANISM: Artificial Sequence
<220> FEATURE:
<223> OTHER INFORMATION: sequence of region 1 in RepB of pTB6

<400> SEQUENCE: 11

```
Phe Cys Arg Leu Leu Gly Val Pro Pro Ser Ala Ile Thr Gln Thr Arg
 1               5                  10                  15

Tyr Leu Asn Gln Lys Val Leu Gln Pro Ile Gln Glu Glu Cys Gly Pro
            20                  25                  30
```

<210> SEQ ID NO 12
<211> LENGTH: 32
<212> TYPE: PRT
<213> ORGANISM: Artificial Sequence
<220> FEATURE:
<223> OTHER INFORMATION: sequence of region 1 in RepB of pJK36 and pB44

<400> SEQUENCE: 12

```
Phe Cys Arg Leu Leu Gly Val Ser Asp Ser Thr Ala Lys Ser Thr Ala
 1               5                  10                  15

Asn Leu Asn Arg Val Val Leu Lys Thr Ile Ala Glu Glu Cys Gly Pro
            20                  25                  30
```

<210> SEQ ID NO 13
<211> LENGTH: 32
<212> TYPE: PRT
<213> ORGANISM: Artificial Sequence
<220> FEATURE:
<223> OTHER INFORMATION: sequence of region 1 in RepB of pNAC2 and
      pDOJH10L

<400> SEQUENCE: 13
```
Phe Cys Arg Leu Leu Ser Val Pro Lys Ser Thr Ala Glu Gln Val Arg
 1               5                  10                  15

Asp Leu Asn Lys Arg Val Leu Lys Pro Ile Ile Glu Glu Cys Gly Pro
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: sequence of region 1 in RepB of pBL01

<400> SEQUENCE: 14

Phe Cys Arg Leu Leu Asn Val Ser Lys Ser Thr Ser Asp Ser Val Ser
 1               5                  10                  15

Asn Leu Asn Arg Val Val Leu Lys Pro Ile Val Glu Glu Cys Gly Pro
            20                  25                  30

<210> SEQ ID NO 15
<211> LENGTH: 16
<212> TYPE: PRT
<213> ORGANISM: Artificial Sequence
<220> FEATURE:
<223> OTHER INFORMATION: sequence of region 2 in RepB of pTB6

<400> SEQUENCE: 15

Val Glu Ala Arg Lys Thr Asp Gly Asp Gly Lys Gly His Trp Thr Ser
 1               5                  10                  15

<210> SEQ ID NO 16
<211> LENGTH: 16
<212> TYPE: PRT
<213> ORGANISM: Artificial Sequence
<220> FEATURE:
<223> OTHER INFORMATION: sequence of region 2 in RepB of pJK36 and pB44

<400> SEQUENCE: 16

Val Glu Ala Arg Lys Thr Asp Gly Asp Gly Lys Gly His Trp Thr Ser
 1               5                  10                  15

<210> SEQ ID NO 17
<211> LENGTH: 14
<212> TYPE: PRT
<213> ORGANISM: Artificial Sequence
<220> FEATURE:
<223> OTHER INFORMATION: sequence of region 2 in RepB of pNAC2 and
      pDOJH10L

<400> SEQUENCE: 17

Val Glu Ala Arg Lys Ala Glu Asp Ala Gly His Trp Thr Ser
 1               5                  10

<210> SEQ ID NO 18
<211> LENGTH: 14
<212> TYPE: PRT
<213> ORGANISM: Artificial Sequence
<220> FEATURE:
<223> OTHER INFORMATION: sequence of region 2 in RepB of pBL01

<400> SEQUENCE: 18

Val Lys Ala Lys Glu Glu Gln Asp Ser Gly His Trp Thr Ser
 1               5                  10

<210> SEQ ID NO 19
<211> LENGTH: 22
<212> TYPE: DNA
<213> ORGANISM: Artificial Sequence
```

```
<220> FEATURE:
<223> OTHER INFORMATION: nt sequence of DR in oriV of pTB6

<400> SEQUENCE: 19
aacctacacc aaaagggag cg                                              22

<210> SEQ ID NO 20
<211> LENGTH: 22
<212> TYPE: DNA
<213> ORGANISM: Artificial Sequence
<220> FEATURE:
<223> OTHER INFORMATION: nt sequence of DR in oriV of pJK36 and pB44

<400> SEQUENCE: 20
acttagtaca aaagggagc ga                                              22

<210> SEQ ID NO 21
<211> LENGTH: 22
<212> TYPE: DNA
<213> ORGANISM: Artificial Sequence
<220> FEATURE:
<223> OTHER INFORMATION: nt sequence of DR in oriV of pNAC2 and pDOJH10L

<400> SEQUENCE: 21
ggggacaaaa agggagcgaa cc                                             22

<210> SEQ ID NO 22
<211> LENGTH: 22
<212> TYPE: DNA
<213> ORGANISM: Artificial Sequence
<220> FEATURE:
<223> OTHER INFORMATION: nt sequence of DR in oriV of pBLO1

<400> SEQUENCE: 22
tgagatcaaa ataggagcgr ay                                             22

<210> SEQ ID NO 23
<211> LENGTH: 24
<212> TYPE: DNA
<213> ORGANISM: Artificial Sequence
<220> FEATURE:
<223> OTHER INFORMATION: nt sequence of IR in oriV of pTB6

<400> SEQUENCE: 23
aaaaaggcgc tgtgcgccct tttt                                           24

<210> SEQ ID NO 24
<211> LENGTH: 24
<212> TYPE: DNA
<213> ORGANISM: Artificial Sequence
<220> FEATURE:
<223> OTHER INFORMATION: nt sequence of DR in oriV of pJK36 and pB44

<400> SEQUENCE: 24
aaaaaggcgc cgtgcgccct tttt                                           24

<210> SEQ ID NO 25
<211> LENGTH: 24
<212> TYPE: DNA
<213> ORGANISM: Artificial Sequence
<220> FEATURE:
<223> OTHER INFORMATION: nt sequence of DR in oriV of pNAC2 and pDOJH10L

<400> SEQUENCE: 25
aaaaaggcgc tttgcgccct ttta                                           24
```

```
<210> SEQ ID NO 26
<211> LENGTH: 27
<212> TYPE: PRT
<213> ORGANISM: Artificial Sequence
<220> FEATURE:
<223> OTHER INFORMATION: aa 1 to 27 of MobA of pBL01

<400> SEQUENCE: 26

Met Ala Ile Tyr His Leu Ser Val Ser Asn Val Ser Arg Ala Ser Gly
 1               5                  10                  15

Ser Arg Ala Thr Ala Thr Leu Ser Tyr Ile Thr
            20                  25

<210> SEQ ID NO 27
<211> LENGTH: 27
<212> TYPE: PRT
<213> ORGANISM: Artificial Sequence
<220> FEATURE:
<223> OTHER INFORMATION: aa 1 to 27 of Mob-sigma line plasmid RSF1010
      (Deposition No. M28829)

<400> SEQUENCE: 27

Met Ala Ile Tyr His Leu Thr Ala Lys Thr Gly Ser Arg Ser Gly Gly
 1               5                  10                  15

Gln Ser Ala Arg Ala Lys Ala Asp Tyr Ile Gln
            20                  25

<210> SEQ ID NO 28
<211> LENGTH: 25
<212> TYPE: PRT
<213> ORGANISM: Artificial Sequence
<220> FEATURE:
<223> OTHER INFORMATION: aa 121 to 145 of MobA of pTB6

<400> SEQUENCE: 28

Thr Tyr Ala Ile His Glu Asp Arg Glu Gly Asn Asn Pro His Ala His
 1               5                  10                  15

Ile Leu Val Ala Asn Arg Gln Ile Asp
            20                  25

<210> SEQ ID NO 29
<211> LENGTH: 24
<212> TYPE: PRT
<213> ORGANISM: Artificial Sequence
<220> FEATURE:
<223> OTHER INFORMATION: aa 108 to 131 of Mob-sigma line plasmid RSF1010
      (Deposition No. M28829)

<400> SEQUENCE: 29

Thr Leu Ala Ile His Ala Gly Gly Gly Glu Asn Pro His Cys His Leu
 1               5                  10                  15

Met Ile Ser Glu Arg Ile Asn Asp
            20

<210> SEQ ID NO 30
<211> LENGTH: 57
<212> TYPE: DNA
<213> ORGANISM: Artificial Sequence
<220> FEATURE:
<223> OTHER INFORMATION: nt 3454 to 3510 of putative oriV of pTB6

<400> SEQUENCE: 30
ccggagggcg cgcttacgga aaatgcaacc tccggttgca tgtaagtgcg ccctaat      57

<210> SEQ ID NO 31
<211> LENGTH: 38
```

```
<212> TYPE: DNA
<213> ORGANISM: Artificial Sequence
<220> FEATURE:
<223> OTHER INFORMATION: nt 3169 to 3132 of oriV of RSF1010

<400> SEQUENCE: 31
ccagtttctc gaagagaaac cggtaagtgc gccctccc                              38
```

SHUTTLE VECTOR FOR *BIFIDOBACTERIUM* AND *ESCHERICHIA COLI*

This application is a national phase application under 35 U.S.C. §371 of International Application No. PCT/JP2005/021566, filed Nov. 24, 2005, entitled "Novel Shuttle Vector" which claims the benefit of Japanese Patent Application No. 2004-339677, filed Nov. 24, 2004.

TECHNICAL FIELD

The present invention relates to a shuttle vector for a microorganism of the genus *Bifidobacterium* and *Escherichia coli*; an expression vector capable of expressing a desired gene in a microorganism of the genus *Bifidobacterium* by use of the shuttle vector; a microorganism of the genus *Bifidobacterium* transformed with the expression vector; and an antitumor agent comprising the microorganism of the genus *Bifidobacterium* as an active ingredient.

BACKGROUND ART

*Bifidobacterium longum* is a Gram-positive anaerobic bacterium and which has a genome with a high GC content (see e.g., Non-Patent Document 1). This *Bifidobacterium longum* is nonpathogenic and constitutes the most part of normal microflora in the large intestines of humans and other animals (see e.g., Non-Patent Document 2). This microorganism is said to have properties of promoting host's health such as enhancement of immunoreaction (see e.g., Non-Patent Document 3), inhibitory effect on the onset of cancer (see e.g., Non-Patent Document 4), protection of hosts against viral infection (see e.g., Non-Patent Documents 5 and 6), and possibility of producing antibacterial substance (see e.g., Non-Patent Document 7). Some microorganisms of the genus *Bifidobacterium* are widely used in the world in the preparation of fermented dairy products.

Furthermore, plasmids of *Bifidobacterium* are expected to be applied to probiotics vectors and oral vaccine vectors against infectious disease. Recent reports have revealed that *Bifidobacterium longum* is accumulated in hypoxic solid tumor after systemic administration (see e.g., Non-Patent Documents 8 and 9), and that a recombinant plasmid pBLES100-S-eCD that bears *Escherichia coli* codA fused with a *Bifidobacterium longum* hup promoter expresses cytosine deaminase in microorganisms (see e.g., Patent Document 1 and Non-Patent Documents 10 and 11). This confirmed the theory that recombinant *Bifidobacterium longum* is effective for enzyme-prodrug therapy. However, while these plasmids are getting attention in the fields of foods, pharmaceutical drugs, and industry, their genetic properties are little known due to the lack of an efficient replicable gene transfer system.

pBLES100, which was used in the construction of the recombinant plasmid pBLES100-S-eCD, is a shuttle vector constructed from the plasmid pTB6 of a *Bifidobacterium longum* BK51 and the plasmid pBR322 of *Escherichia coli* (see e.g., Non-Patent Document 12). This shuttle vector pBLES100 transformed *Bifidobacterium longum* at an efficiency of $2.2 \times 10^4$ transformants/µg DNA and was stable in the cells in terms of structure and segregation of phenotypes (see e.g., Non-Patent Document 13). However, as the plasmid having unmodified DNA can be cleaved with a restriction enzyme in the microorganism during transfection, cloning of a foreign gene requires higher transformation efficiency.

Patent Document 1: Japanese Laid-Open Patent Application No. 2002-97144

Non-Patent Document 1: Scardovi, Bergey's Manual of Systematic Bacteriology vol 2, eds. Sneath et al., pp. 1418-1434 (1986)

Non-Patent Document 2: Mitsuoka, Elsevier Applied Science, pp 69-114 (1992)

Non-Patent Document 3: Yasui et al., J. Dairy Sci., 74, 1187-1195 (1991)

Non-Patent Document 4: Reddy et al., Cancer Res., 53, 3914-3918 (1993)

Non-Patent Document 5: Duffy et al., Pediatr. Res., 35, 690-695 (1994)

Non-Patent Document 6: Saaverdra et al., Lancet., 344, 1046-1049 (1994)

Non-Patent Document 7: Ibrahim et al., J. Food Prot., 56, 713-715 (1993)

Non-Patent Document 8: Yazawa et al., Cancer Gene Ther., 7, 269-274 (2000)

Non-Patent Document 9: Yazawa et al., Breast Cancer Res. Treat., 66, 165-170 (2001)

Non-Patent Document 10: Nakamura et al., Biosci. Biotechnol. Biochem., 66, 2362-2366 (2002)

Non-Patent Document 11: Fujimori et al., Curr. Opin. Drug Discov. Devel., 5, 200-203 (2002)

Non-Patent Document 12: Matsumura et al., Biosci. Biotechnol. Biochem., 61, 1211-1212 (1997)

Non-Patent Document 13: Matsumura et al., Biosci. Biotechnol. Biochem., 61, 1211-1212 (1997)

DISCLOSURE OF THE INVENTION

Problem to be Solved by the Invention

As described above, a shuttle vector pBLES100 for a microorganism of the genus *Bifidobacterium* and *Escherichia coli* transformed *Bifidobacterium longum* at an efficiency of $2.2 \times 10^4$ transformants/µg DNA and was stable in the cells in terms of structure and segregation of phenotypes. However, as the plasmid having unmodified DNA can be cleaved with a restriction enzyme in the microorganism during transfection, cloning of a foreign gene requires higher transformation efficiency. The object of the present invention is to provide a shuttle vector for a microorganism of the genus *Bifidobacterium* and *Escherichia coli* having a wide host range and a large copy number in microorganisms of the genus *Bifidobacterium* and capable of highly expressing a desired protein in a microorganism of the genus *Bifidobacterium* when used as an expression vector; an expression vector capable of expressing a desired gene in a microorganism of the genus *Bifidobacterium* by use of the shuttle vector; a microorganism of the genus *Bifidobacterium* transformed with the expression vector; and an antitumor agent comprising the microorganism of the genus *Bifidobacterium* as an active ingredient.

Means to Solve the Problems

The present inventors determined the complete sequence (3624 bp; SEQ ID NO: 1) of a plasmid pTB6 derived from *Bifidobacterium longum* BK51 and identified some gene sequences of this microorganism of the genus *Bifidobacterium* including the plasmid replication origin OriV. The present inventors found out that OriV is a 358-bp sequence containing dso and sso, and that a pTB6-derived fragment of approximately 1900 by in full length containing a replication protein (RepB, 693 bp) is available as a "replication unit of a microorganism of the genus *Bifidobacterium*." Replication ability was not confirmed for a unit containing OriV and a portion of RepB. The present inventors completed the present invention by finding out that the expression of an expression product of an ampicillin resistance gene serving as a selective marker, particularly the expression of the N-terminal region thereof, is unfavorable in terms of expansion of a host range in microorganisms of the genus *Bifidobacterium*.

Namely, the present invention relates to (1) a shuttle vector for a microorganism of the genus *Bifidobacterium* and *Escherichia coli* characterized by comprising a pTB6-derived region portion comprising a replication origin (oriV)-repB region of pTB6 but not comprising MembB, MobA, OrfI, and oriT regions of pTB6 and an *Escherichia coli*-derived plasmid portion comprising pUC ori; (2) the shuttle vector for a microorganism of the genus *Bifidobacterium* and *Escherichia coli* according to (1), wherein the pTB6-derived region portion consists of a TB6-derived region portion comprising a 1260-bp nucleotide sequence consisting of a nucleotide sequence represented by nucleotides 305 to 1564 in SEQ ID NO: 1; (3) the shuttle vector for a microorganism of the genus *Bifidobacterium* and *Escherichia coli* according to (1) or (2), wherein the *Escherichia coli*-derived plasmid portion comprising pUC ori is a plasmid portion not comprising an ampicillin resistance gene (ampR) or having deleted DNA encoding an N-terminal region of an ampicillin resistance gene (ampR) expression product β-lactamase; (4) the shuttle vector for a microorganism of the genus *Bifidobacterium* and *Escherichia coli* according to any one of (1) to (3), wherein the microorganism of the genus *Bifidobacterium* is *Bifidobacterium longum, Bifidobacterium breve, Bifidobacterium animalis, Bifidobacterium bifidum*, or *Bifidobacterium adolescentis*; (5) the shuttle vector for a microorganism of the genus *Bifidobacterium* and *Escherichia coli* according to any one of (1) to (4), wherein the shuttle vector has an average copy number of 6 to 30; (6) the shuttle vector for a microorganism of the genus *Bifidobacterium* and *Escherichia coli* according to any one of (1) to (5), wherein the shuttle vector is pAV001; (7) an expression vector capable of expressing a desired gene in a microorganism of the genus *Bifidobacterium*, comprising the shuttle vector for a microorganism of the genus *Bifidobacterium* and *Escherichia coli* according to any one of (1) to (6) into which an expression unit of the desired gene ligated in-frame between a promoter and a terminator involved in the expression of a *Bifidobacterium* longum-derived gene encoding a histone-like DNA-binding protein (HU protein) is inserted; (8) the expression vector according to (7), wherein the desired gene is a cytosine deaminase gene; (9) a microorganism of the genus *Bifidobacterium* transformed with the expression vector according to (7) or (8); (10) an antitumor agent comprising the microorganism of the genus *Bifidobacterium* according to (9) as an active ingredient; (11) a pTB6-derived plasmid replication unit of a microorganism of the genus *Bifidobacterium* comprising a replication origin (oriV)-repB region of pTB6 but not comprising MembB, MobA, OrfI, and oriT regions of pTB6; and (12) the pTB6-derived plasmid replication unit of a microorganism of the genus *Bifidobacterium* according to claim 11, comprising a 1260-bp nucleotide sequence consisting of a nucleotide sequence represented by nucleotides 305 to 1564 in SEQ ID NO: 1.

BRIEF DESCRIPTION OF DRAWINGS

[FIG. 1]
FIG. 1 is a diagram showing a linear map of a plasmid pTB6 (3624 bp) and the structure of oriV. FIG. 1(*a*) represents putative RepB, MembB, MobA, and a putative protein OrfI. The arrows denote the of translation, and the numerals denote nucleotide position. FIG. 1(*b*) schematically represents 2 sets of IR (305 to 417) in sso and 1 set of IR (481 to 504) and 4 repeat units (indicated by the triangles) (577 to 664) in dso located in oriV. The diagram is indicated without reference to scale.

[FIG. 2]
FIG. 2 is a diagram showing sequences in RepB and oriT. The amino acid sequences (a) of region 1 (region 1 of pTB6 corresponds to SEQ ID NO:11; region 1 of pKJ36, pB44 corresponds to SEQ ID NO:12; region 1 of pNAC2, pDOJH1OL corresponds to SEQ ID NO:13; region 1 of pBLO1 corresponds to SEQ ID NO:14) for p and region 2 (region 2 of pTB6 corresponds to SEQ ID NO:15; region 2 of pKJ36, pB44 corresponds to SEQ ID NO:16; region 2 of pNAC2, pDOJH1OL corresponds to SEQ ID NO:17; region 2 of pBLO1 corresponds to SEQ ID NO:18) in RepB and the nucleotide sequences of DR (DR of pTB6 corresponds to SEQ ID NO:19; DR of pKJ36, pB44 corresponds to SEQ ID NO:20; DR of pNAC2, pDOJH1OL corresponds to SEQ ID NO:21; DR of pBLO1 corresponds to SEQ ID NO:22) (b) and IR (IR of pTB6 corresponds to SEQ ID NO:23; IR of pKJ36, pB44, pNAC2, pDOJH1OL corresponds to SEQ ID NO:24; IR of pBLO1 corresponds to SEQ ID NO:25) (c) in oriV are arranged in the diagram. The numerals above the sequence denote amino acid position in predicted RepB of pTB6 , and the numerals above the dotted line denote the number of amino acids in the regions. The nucleotide (nuc) position in FIG. 2(*b*) denotes the gene locus of DR, and the nucleotide sequences of the repeat units are arranged. The nucleotide (nuc) position in FIG. 2(*c*) denotes the gene locus of IR, and their sequences are arranged. The rectangles overlaid with dots represent the conserved regions of the amino acids or the nucleotides.

[FIG. 3]
FIG. 3 is a diagram showing an amino acid sequence in MobA and a nucleotide sequence in oriV. In FIG. 3(*a*), the partial amino acid sequences (amino acids 1 to 27 (SEQ ID NO:26) and 121 to 145 (SEQ ID NO:27)) of MobA of pTB6 and the partial amino acid sequences (amino acids 1 to 27 (SEQ ID NO:28) and 108 to 131 (SEQ ID NO:29)) of a MOBo-line plasmid RSF1010 (Deposition No. M28829) are arranged. The symbol * denotes an active Tyr associated with DNA nicking-closing activity in Motif I and 3H motif in Motif III. In FIG. 3(*b*), the nucleotide sequence of nucleotides 3454 to 3510 (SEQ ID NO:30) of putative oriV of pTB6 and the nucleotide sequence at position 3169 to 3132 (SEQ ID NO:31) of oriT of RSF1010 are arranged. The arrows denote characteristic IR, and the arrowhead denotes a nicking (nic) site by MobA of RSF1010. The numerals above and below the sequences denote the amino acid position of MobA or the nucleotide position of pTB6. The regions indicated by the rectangles overlaid with dots denote nucleotide sequences homologous with matched amino acids.

[FIG. 4]
FIG. 4 is a diagram showing linear maps of reconstituted plasmids. The PstI-FspI fragment of pTB6 (nucleotides 1 to 1872) was inserted into the PstI-FspII site of pUC18 to obtain a composite plasmid. The 1.6 kbp-HincII-HindIII fragment containing spc of pBLES100 was ligated with the HindIII-SspI fragment (4.0 kbp) and the HindIII-FspI fragment (3.4 kbp) of the composite plasmid to obtain pBRASTA100 (5.6 kbp) and pBRASTA101 (5.0 kbp), respectively. The 0.6 kbp-SspI-FspI fragment (indicated by the rectangle with a short underline and a shading line) of pUC18 was inserted into the BamHI site and the BamHI and HindIII sites of pBRASTA101 to obtain pBRASTA102 (5.6 kbp) and pBRASTA103 (6.2 kbp), respectively. A plasmid pSS030Sp (5.4 kbp) was constructed by the same procedure as in the construction of pBRASTA100 except that the PstI-FspI DNA fragment (nucleotides 1873 to 3624) of pTB6 instead of the PstI-FspI DNA fragment (nucleotides 1 to 1872) was inserted into the PstI-HincII site of pUC18. The AatII-EcoRV fragment containing spc (1.3 kbp) of pBLES100 was ligated to a recombinant molecule AatII-FspI fragment (1.4 kbp) constructed by inserting the DNA fragment (nucleotides 472 to 1872) of pTB6 into the AatII-HincII site of pUC18, to construct a plasmid pDSO44Sp (4.3 kbp). The rectangles with a shading line denote sso and dso. The diagram is indicated without reference to scale.

[FIG. 5]

FIG. 5 is a diagram showing the production processes of *Bifidobacterium longum*::pAV001-HU-eCD and *Bifidobacterium longum*::pBLES100-S-eCD.

[FIG. 6]

FIG. 6 is a diagram showing the comparison result of the expression level of a cytosine deaminase protein in *Bifidobacterium longum*. The diagram shows that the cytosine deaminase protein is expressed 2 to 8-fold by *Bifidobacterium longum*::pAV001-HU-eCD compared to that expressed by *Bifidobacterium longum*::pBLES100-S-eCD.

[FIG. 7]

FIG. 7 is a diagram showing a temporal shift in bacterial counts obtained by a result of comparison of enzyme activity of the cytosine deaminase protein (comparison of activity of converting 5FC to 5FU) in *Bifidobacterium longum*.

[FIG. 8]

FIG. 8 is a diagram showing a 5-FU concentration obtained by a result of comparison of enzyme activity of the cytosine deaminase protein (comparison of activity of converting 5FC to 5FU) in *Bifidobacterium longum*.

[FIG. 9]

FIG. 9A is a diagram showing a result of Southern analysis, after culturing *Bifidobacterium longum*::pAV001-HU-eCD and *Bifidobacterium longum*::pBLES100-S-eCD, digesting DNAs extracted from the respective bacterial cells with a restriction enzyme, and separating nucleic acids by agarose gel electrophoresis to subject to Southern analysis using Alk-Phos Direct Labelling. Reagents (Amersham Bioscience). FIG. 9B is a diagram showing the comparison result of plasmid copy numbers of *Bifidobacterium longum*::pAV001-HU-eCD and *Bifidobacterium longum*::pBLES100-S-eCD on the basis of signal intensity.

BEST MODE OF CARRYING OUT THE INVENTION

A shuttle vector for a microorganism of the genus *Bifidobacterium* and *Escherichia coli* of the present invention is not particularly limited as long as it is a shuttle vector comprising a pTB6-derived region portion comprising a replication origin (oriV; nucleotides 305 to 664 in a nucleotide sequence represented by SEQ ID NO: 1)-repB (nucleotides 872 to 1564 in the nucleotide sequence represented by SEQ ID NO: 1) region of pTB6 but not comprising MembB (nucleotides 1543 to 2355 in the nucleotide sequence represented by SEQ ID NO: 1), MobA (nucleotides 2212 to 3300 in the nucleotide sequence represented by SEQ ID NO: 1), OrfI (nucleotides 3587 to 517 in the nucleotide sequence represented by SEQ ID NO: 1), and oriT (nucleotides 3454 to 3510 in the nucleotide sequence represented by SEQ ID NO: 1) regions of pTB6 and an *Escherichia coli*-derived plasmid portion comprising pUC ori. However, a replication unit comprising a 1260-bp nucleotide sequence consisting of a nucleotide sequence represented by nucleotides 305 o 1564 in SEQ ID NO: 1, for example, a 1260-bp minimum replication unit consisting of a nucleotide sequence represented by nucleotides 305 to 1564 in SEQ ID NO: 1, a 1900-bp replication unit consisting of a nucleotide sequence represented by nucleotides 1 to 1900 in SEQ ID NO: 1, and a 2355-bp maximum replication unit consisting of a nucleotide sequence represented by nucleotides 1 to 2355 in SEQ ID NO: 1, are preferable. Thus, by using a smaller replication unit without the MemB, MobA, OrfI, and OriT regions, the copy number in host cells can be increased. It is preferred that the shuttle vector has a copy number larger than that of a shuttle vector pBLES 100 for *Bifidobacterium longum* and *Escherichia coli* that can be constructed by the method described in Biosci. Biotech. Biochem., 61, 1211 (1997), and has an average copy number increased of, for example, 3 to 20, particular preferably 6 to 30.

In the shuttle vector of the present invention, it is preferred that the *Escherichia coli*-derived plasmid portion comprising pUC ori does not comprise an ampicillin resistance gene (ampR) or, if any, a portion wherein DNA encoding the N-terminal region of its expression product β-lactamase is deleted is preferable. The expression lacking the N-terminal region of β-lactamase allows for the expansion of a host range in microorganisms of the genus *Bifidobacterium*.

In the shuttle vector of the present invention, the microorganism of the genus *Bifidobacterium* can concretely be exemplified by *Bifidobacterium longum*, *Bifidobacterium adolescentis*, *Bifidobacterium breve*, *Bifidobacterium animalis*, and *Bifidobacterium bifidum*. In contrast, the replication of the shuttle vector pBLES100 in microorganisms of the genus *Bifidobacterium* other than *Bifidobacterium longum* is not confirmed.

The shuttle vector of the present invention can preferably be exemplified by the shuttle vector pAV001 described in Example 2.

A pTB6-derived plasmid replication unit of a microorganism of the genus *Bifidobacterium* of the present invention is not particularly limited as long as it is a pTB6-derived region portion comprising a replication origin (oriV; nucleotides 305 to 664 in the nucleotide sequence represented by SEQ ID NO: 1)-repB (nucleotides 872 to 1564 in the nucleotide sequence represented by SEQ ID NO: 1) region of pTB6 but not comprising MembB (nucleotides 1543 to 2355 in the nucleotide sequence represented by SEQ ID NO: 1), MobA (nucleotides 2212 to 3300 in the nucleotide sequence represented by SEQ ID NO: 1), OrfI (nucleotides 3587 to 517 in the nucleotide sequence represented by SEQ ID NO: 1), and oriT (nucleotides 3454 to 3510 in the nucleotide sequence represented by SEQ ID NO: 1) regions of pTB6. The plasmid replication unit can preferably be exemplified by a replication unit comprising a 1260-bp nucleotide sequence consisting of a nucleotide sequence represented by nucleotides 305 to 1564 in SEQ ID NO: 1, for example, a 1260-bp minimum replication unit consisting of a nucleotide sequence represented by nucleotides 305 to 1564 in SEQ ID NO: 1, a 1900-bp replication unit consisting of a nucleotide sequence represented by nucleotides 1 to 1900 in SEQ ID NO: 1, and a 2355-bp maximum replication unit consisting of a nucleotide sequence represented by nucleotides 1 to 2355 in SEQ ID NO: 1.

An expression vector of the present invention capable of expressing a desired gene in a microorganism of the genus *Bifidobacterium* is not particularly limited as long as it is a vector comprising the shuttle vector for a microorganism of the genus *Bifidobacterium* and *Escherichia coli* of the present invention into which an expression unit of the desired gene ligated in-frame between a promoter and a terminator involved in the expression of *Bifidobacterium longum*-derived gene encoding a histone-like DNA-binding protein (HU protein) is inserted. The desired gene is not particularly limited and can preferably be exemplified by a gene encoding a cytokine or angiogenic inhibitor having antitumor activity and a gene encoding an enzyme capable of converting a low toxic antitumor substance precursor to an antitumor substance (hereinafter, abbreviated to as a converting enzyme).

The promoter and the terminator in the expression unit can preferably be exemplified by a DNA represented by nucleotides 1 to 192 and DNA represented by nucleotides 472 to 600, respectively, in the nucleotide sequence that can be represented by SEQ ID NO: 2. The expression vector having the promoter and the terminator involved in the expression of a HU gene can be prepared by cleaving a HU gene with a restriction enzyme from the DNA of *Bifidobacterium longum*, then incorporating the HU gene into a cloning vector, and further incorporating the desired gene to the downstream of the promoter involved in the expression of the HU gene. The desired gene can be expressed efficiently by using the promoter and the terminator involved in the expression of the HU gene. Examples of a method for isolating the HU gene include a method digesting the chromosomal DNA of *Bifidobacterium longum* with the restriction enzyme HindIII. To be more specific, the chromosomal DNA of *Bifidobacterium longum* is first digested with a restriction enzyme HindIII and then purified by phenol treatment and ethanol precipitation. On the other hand, pBR322 (TAKARA SHUZO) is also digested with HindIII and subjected to dephosphorylation treatment, followed by purification in the same way. The respective DNAs are ligated to obtain recombinant DNA. Next, the recombinant DNA is used to transform *Escherichia coli* mH3 (Gene, 45, 37 (1986)) according to a conventional method to obtain a transformant exhibiting ampicillin resistance and tetracycline sensitivity. Plasmid DNA is extracted from the obtained transformant according to a conventional method and introduced into an *Escherichia coli* YK2741 strain (Gene, 89, 133 (1990)) according to a conventional method to transform the bacterial strain. The YK2741 strain, which has HU and IHF (integration host factor) genes deleted, exhibits cold sensitivity, and with this property the transformant is selected by plating onto an ampicillin-containing agar medium and culturing at 27° C. Subsequently, the transformant of the YK2741 strain thus obtained is further cultured, and plasmid retained in the strain is extracted according to a conventional method and introduced into *Escherichia coli* YK1340 (J. Mal. Biol., 204, 581 (1988)) according to a conventional method to transform the bacterial strain. The obtained transformant is subjected to an infection test with Mu phage according to a conventional method. The YK1340 strain is a HU genes-deleted strain, and as the proliferation of the Mu phage requires HU proteins, a transformant that is lysed by Mu phage infection and proliferation can be a potent candidate of a strain bearing the *Bifidobacterium longum*-derived HU gene. Thus, the plasmid pBLHU15 having the promoter and the terminator involved in the expression of the *Bifidobacterium longum*-derived HU gene can be obtained by selecting a plasmid retained in the strain exhibiting ampicillin resistance and is lysed by Mu phage infection and proliferation. Moreover, a site developed by using NsvV and HpaI is preferable as an introduction site of the desired gene.

For the gene encoding a cytokine having antitumor activity, examples include interferon (IFN)-α, IFN-β, IFN-γ, granulocyte-macrophage colony stimulating factor (GM-CSF), interleukin (IL)-1α, Il-β, IL-2, IL-3, IL-4, IL-6, IL-7, IL-10, IL-12, IL-13, IL-15, IL-18, IL-27, tumornecrosis factor (TNF)-α, lymphotoxin (LT)-β, granulocyte colony stimulating factor (G-CSF), macrophage colony stimulating factor (M-CSF), macrophage migration inhibitory factor (MIF), leukemia inhibitory factor (LIF), co-stimulatory factors B7 (CD80) and B7-2 (CD86) for T-cell activation, Kit ligand, and oncostatin M. Particularly, IL-2 is preferable. Alternatively, these cytokines may be used in combination of two or more of them, and, for example, the combination of IL-6 with TNF-α, IFN-α, IFN-β, or IFN-γ, the combination of TNF-α with IFN-γ, and the combination of anti-Fas with IFN-γ are preferable. Angiogenic inhibitors such as endostatin, angiostatin, kringle 1, kringle 2, kringle 3, kringle 4, kringle 5, and NK4 can be used advantageously as substances having antitumor activity other than the cytokine.

Examples of the gene encoding a converting enzyme include: a combination of 5-fluorocytosine (5-FC) as an antitumor substance precursor, 5-fluorouracil (5-FU) as an antitumor substance, and cytosine deaminase as a converting enzyme; a combination of 5-aziridino-2,4-dinitrobenzamide (CB1954) as an antitumor substance precursor, an alkylating agent known to cause bridge bond in double-stranded DNA as an antitumor substance, and nitroreductase as a converting enzyme; and a combination of ganciclovir as an antitumor substance precursor, a metabolite thereof as an antitumor substance, and herpes simplex virus type 1 thymidine kinase (HSV1-TK) as a converting enzyme. In addition, by converting an antitumor substance into a precursor (including an inactivated product) low toxic to human bodies by modification such as glucuronide conjugation, glycine conjugation, or lysine conjugation, and the enzyme that demodifies the precursor can be used as a converting enzyme. Any of known per se in the art may be used as enzyme that demodifies the precursor. For example, the combination of a glucuronide-conjugated antitumor substance precursor with β-glucuronidase as a converting enzyme can be exemplified.

The microorganism of the genus *Bifidobacterium* of the present invention is not particularly limited as long as it is a microorganism of the genus *Bifidobacterium* transformed with the expression vector of the present invention. Concrete examples thereof include *Bifidobacterium longum*, *Bifidobacterium adolescentis*, *Bifidobacterium bifidum*, *Bifidobacterium pseudolongum*, *Bifidobacterium thermophirum*, *Bifidobacterium breve*, *Bifidobacterium infantis*, and *Bifidobacterium animalis*. Among these, *Bifidobacterium longum*, *Bifidobacterium adolescentis* *Bifidobacterium bifidum*, or *Bifidobacterium infantis* known to inhabit in the intestines of humans regardless of age, are preferable, and *Bifidobacterium longum*, is more preferable. All of these bacteria are commercially available or can be obtained easily from depository institutions. For example, *Bifidobacterium longum* ATCC-15707, *Bifidobacterium bifidum* ATCC-11863, and *Bifidobacterium infantis* ATCC-15697 can be used.

The plasmid replication unit, the shuttle vector, the expression vector, and the transformed microorganism of the genus *Bifidobacterium* of the present invention can be prepared according to the methods described in commercially available experiment manuals, for example, Gene Manual (Kodansha), Methods for Experiments in Gene Manipulation (ed., Yasutaka Takagi, Kodansha), Molecular Cloning (Cold Spring Harbor Laboratory (1982)), Molecular Cloning, 2nd ed. (Cold Spring Harbor Laboratory (1989)), Methods in Enzymology, 194 (1991), and Gene Experiments Using Yeasts, Experimental Medicine Suppl. (Yodosha (1994)).

The transformed microorganism of the genus *Bifidobacterium* can proliferate only in tumor tissues under anaerobic environment and express substances having antitumor activity, converting enzymes and the like, in the tumor tissues.

Thus, the transformed microorganism of the genus *Bifidobacterium* is used as a medicine effective for treating tumor having anaerobic environment, preferably solid tumor. The antitumor agent of the present invention is not particularly limited as long as it comprises the microorganism of the genus *Bifidobacterium* of the present invention as an active ingredient. The administration of the antitumor agent of the present invention is not particularly limited and include oral administration and parenteral administration, while parenteral administration is particularly preferable. Examples of parenteral administration can include airway, intrarectal, subcutaneous, intramuscular, and intravenous administration. Examples of preparations suitable for oral administration include tablets, granules, fine granules, powders, syrups, solutions, capsules, and suspensions. Examples of preparations suitable for parenteral administration include injections, infusions, inhalants, propellants, suppositories, transdermal absorbents and transmucosal absorbents. In the present invention, it is preferred that the preparations are used as injections, particularly intravenous injections.

The transformed microorganism of the genus *Bifidobacterium* may be supplied to aftertreatment known per se in the art. For example, partial purification can be performed by centrifugation. Moreover, after partial purification, the microorganism may then be dissolved or suspended, in a solvent conventionally used in the art such as saline, PBS (phosphate-buffered saline), or lactated Ringer's solution, if desired. Further, lypholization or spray drying can be performed to make powdered or granulated product, if desired.

The solution or suspension of the transformed microorganism of the genus *Bifidobacterium* or the dried powdered or granulated product of the transformed microorganism may be administered directly as the antitumor agent of the present invention. However, it is generally desirable that the antitumor agent is administered in the form of a pharmaceutical composition comprising the above substances serving as an active ingredient and one or more pharmaceutical additives. Such pharmaceutical compositions can be produced according to a method well known or commonly used per se in the pharmaceutical field.

Examples of pharmaceutical additives that can be used in the production of the liquid preparations suitable for oral administration include: water; saccharides such as cane sugar, sorbit, and fruit sugar; glycols such as polyethylene glycol and propylene glycol; oils such as sesame oil, olive oil, and soybean oil; and preservatives such as p-hydroxybenzoic acid esters. For the production of the solid preparations such as capsules, tablets, powders, and granules include: excipients such as lactose, glucose, cane sugar, and mannite; disintegrants such as starch and sodium alginate; lubricants such as magnesium stearate and talc; binders such as polyvinyl alcohol, hydroxypropylcellulose, and gelatin; surfactants such as fatty acid ester; and plasticizers such as glycerin, can be used.

Of the preparations suitable for parenteral administration, preparations for intravascular administration such as injections and infusions can preferably be prepared by using an aqueous medium isotonic with human blood. For example, injections can be prepared as a solution, suspension, or dispersion together with an appropriate auxiliary according to a conventional method by using an aqueous medium selected from salt solution, glucose solution, or a mixture of salt solution and glucose solution. Suppositories for intestinal administration can be prepared by using a carrier, for example, cocoa butter, hydrogenated fat, or hydrogenated carboxylic acid. Propellants can be prepared by using a carrier that gives no stimulation to human oral cavity and airway mucosa and that can promote absorption of the microorganism of the genus *Bifidobacterium* of the present invention serving as an active ingredient by dispersing the microorganism as fine particles. For example, lactose or glycerin can be used as a carrier. In addition, it can be prepared as preparations in forms of aerosols and dry powders. For example, one or two or more pharmaceutical additives selected from diluents, flavors, preservatives, excipients, disintegrants, lubricants, binders, surfactants, and plasticizers can be used in the production of preparations for parenteral administration. The form and production method of the antitumor agent of the present invention are not limited to the specific examples mentioned above.

The dosage and administration frequency of the antitumor agent of the present invention are not particularly limited and can appropriately be selected according to various conditions such as the type of gene retained in the microorganism of the genus *Bifidobacterium*, the type of a morbid condition to be treated, administration routes, age and body weight of the patient, symptoms, and the severity of disease. For example, when the antitumor agent is systemically administered by intravenous injection, the daily dosage in adult is preferably approximately $2\times10^6$ to $2\times10^7$ microorganisms/body. When the antitumor agent is locally administered into tumor, the dosage is preferably approximately $5\times10^8$ microorganisms/tumor. However, the dosage is not limited to this specific example.

The antitumor agent according to the present invention can be applied to tumor having anaerobic environment, preferably a variety of solid cancers. Examples of solid cancers include large bowel cancer, brain tumor, head and neck cancer, breast cancer, lung cancer, esophagus cancer, gastric cancer, hepatic cancer, gallbladder cancer, bile duct cancer, pancreatic cancer, islet cell cancer, choriocarcinoma, colonic cancer, renal cell carcinoma, adrenal cortical cancer, bladder cancer, testicle cancer, prostate cancer, testicular tumor, ovarian cancer, uterine cancer, choriocarcinoma, thyroid cancer, malignant carcinoid tumor, skin cancer, malignant melanoma, osteosarcoma, soft tissue sarcoma, neuroblastoma, Wilms tumor, retinoblastoma, melanoma, and squamous cell carcinoma.

The medicine of the present invention may be used with other medicines and the like. Particularly, when the microorganism of the genus *Bifidobacterium* incorporating therein the gene encoding a converting enzyme is administered, the administration of an antitumor substance precursor is essential. However, the antitumor substance precursor may form a single preparation together with the microorganism of the genus *Bifidobacterium* incorporating therein the gene encoding a converting enzyme; or otherwise, it may be separate preparations to be administered simultaneously or at time intervals. Moreover, it is preferred to be used with Lactulose. Lactulose is a nutrition source for the microorganism of the genus *Bifidobacterium* and is not metabolized by humans, mice, and pigs. Therefore, by administrating Lactulose, the number of the microorganism of the genus *Bifidobacterium* tumor tissue increases in a specific manner. The daily dosage thereof in adult is preferably approximately 24 to 48 g/body, and the administration frequency is not limited. Moreover, the medicine of the present invention can be used in combination with other antitumor agents and the like.

The microorganism of the genus *Bifidobacterium* of the present invention administered to a patient can be killed easily by an antibiotic. This is important for more enhancing the safety of the gene transfer system according to the present invention.

Hereinafter, the present invention will be described more fully with reference to Examples. However, the technical scope of the present invention is limited to these illustrations.

EXAMPLE 1

Structural Analysis of Plasmid pTB6

[Materials and Method]

1. Bacterial Strains, Plasmids, and Media

Bacterial strains and plasmids used in the present invention are listed in Table 1. *Escherichia coli* was aerobically cultured at 37° C. in LB broth (10 g of Bacto-tryptone, 5 g of yeast extract, 5 g of NaCl, and 0.1% glucose per litter), and colonies were allowed to form in LB broth containing 1.5% agar. *Bifidobacterium longum* 105-A (see Non-Patent Document 12) was anaerobically cultured at 37° C. in MRS broth (Difco Laboratories, USA) supplemented with 50 mM sucrose, 0.34% cysteine, and 0.02% sodium ascorbate. An antibiotic (50 µg/ml ampicillin (Ap) and/or 75 µg/ml spectinomycin (Sp)) was added according to need. Colonies were allowed to form on broth containing 1.5% agar by using Gas-Pak anaerobic system (BL, USA) according to the method described in Non-Patent Document 12.

TABLE 1

Bacterial strains and plasmids used in this study

| Strain or Plasmids | Relevant characteristics | Source or Reference |
|---|---|---|
| Bacterial strains | | |
| E. coli HMS174 | recA1 hsdR ri/Sp$^s$ | Sambrook et al.* |
| B. longum 105-A | Sp$^s$ | Matsumura et al.** |
| Plasmids | | |
| pUC18 | 2.7 kbp; ColE1 ori, amp | Sambrook et al.* |
| pBLES100 | 9.1 kbp; ColE1 ori, whole pTB6, spc | Matsumura et al.** |
| pBRASTA100 | 5.6 kbp; ColE1 ori, pTB6 oriV-repB, spc, amp | This study |
| pBRASTA101 | 5.0 kbp; ColE1 ori, pTB6 oriV-repB, spc, | This study |
| pBRASTA102 | 5.6 kbp; ColE1 ori, pTB6 oriV-repB, spc, | This study |
| pBRASTA103 | 6.2 kbp, ColE1 ori, pTB6 oriV-repB, spc, | This study |
| pDS044Sp | 4.3 kbp; ColE1 ori, pTB6 oriV-repB, Δsso, spc | This study |
| pSS030Sp | 5.4 kbp; ColE1 ori, pTB6 mobA, spc, amp | This study |

*Sambrook, J. E., Fritsch, F., and Maniatis, T., In "Molecular cloning: a laboratory manual" 2nd, eds. Cold Spring Harbor Laboratory, New York, (1989).
**Matsumura, H., Takeuchi, A., ando Kano, Y., Construction of *Escherichia coli-Bifidobacterium longum* shuttle vector transforming *B. longum* 105-A and 108-A. Biosci. Biotechnol. Biochem., 61, 1211-1212(1997).

2. Plasmid DNA Isolation and Molecular Manipulation

Qiagen Plasmid Kit (QIAGEN, USA) was used according to procedures described in the accompanying manual to extract plasmid DNA by a modified alkali lysis method. The *Bifidobacterium longum* was washed with 0.9% NaCl and treated at 37° C. for 30 minutes with lysozyme (1 mg/ml) before alkali lysis and at 37° C. for 15 minutes with proteinase K (0.1 mg/ml) before phenol treatment.

Competent cells of *Bifidobacterium longum* were prepared according to the method described in Non-Patent Document 12. The cells harvested at late log phase were washed three times with 50 mM buffered sucrose solution and were resuspended in ice-cold glycerin (10% v/v) of approximately one hundredth of the volume of the original cultured product. Moreover, competent cells of the *Escherichia coli* were prepared according to the method described previously (Takeuchi et al., Biosci. Biotechnol. Biochem., 66, 598-603 (2002)).

GenePulser apparatus (Bio-Rad Labs., USA) was used under the conditions of 200Ω parallel resistance, 2.5 kV/cm, and 25 µF according to the method described in Non-Patent Document 12 to perform electroporation using 100 ng of the plasmid DNA and 50 µl of the bacterial solutions.

DNA was amplified using GeneAmp PCR System 9600 and LA Taq Polymerase (TAKARA). Two primers [5'-GGC-CGGAATTCTGAGCAAAAGGCCAGCAAAAGGCC-3 (SEQ ID NO: 3) and 5'-GGCCGGAATTCAGTACT-CATATATACTTTAGATTGATTTA-3' (SEQ ID NO: 4)] were used to amplify ColE1 on from pUC18 by PCR. Next, by using two primers [5'-GCGGCGGATCCAT-TGAAAAAGGAAGAGTAT-3' (SEQ ID NO: 5) and 5'-CG-GCCGGATCCTGCGCAACGTTGTTGCCAT-3' (SEQ ID NO: 6)] for constructing pBRASTA102 and two primers [5'-GCGGCAAGCTTATTGAAAAAGGAAGAGTAT-3' (SEQ ID NO: 7) and 5'-CGGCCAAGCTTTGCGCAACGTTGT-TGCCAT-3' (SEQ ID NO: 8)] for constructing pBRASTA103, a half amp region proximal to the promoter was amplified from pUC18. Other DNA manipulations were all performed according to the method described previously (Sambrook et al., Molecular cloning: a laboratory manual 2nd eds. Cold Spring Harbor Laboratory (1989)).

3. DNA Sequencing and Sequence Analysis pBLES100 was cleaved with PstI to prepare the full-length DNA (3.6 kbp) of pTB6. After digestion with Sau3AI or AluI, the DNA was subcloned in the multi-cloning site of pUC18. ALF express II DNA sequencer and Thermo Sequenase Cycle Sequencing Kit or Thermo Sequenase CyTM 5 Dye Terminator Cycle Sequencing Kit (Amersham Pharmacia Biotech) were used to perform sequencing. DNASIS-Mac v2.2 and GENETYX-MAC software were used to practice sequence assembly and sequence analysis using computer. FASTA and BLAST servers were used for homology search.

[Results]

1. Plasmid Structure

The complete nucleotide sequence (3,624 bp) of pTB6 of *Bifidobacterium longum* BK51 serving as a component of the shuttle vector pBLES100 was determined. pTB6 (FIG. 1(a)) was predicted from data base search to contain 4 open reading frames (Orf)), that is, RepB (872 to 1564), MembB (1543 to 2355), MobA (3300 to 2212), and a hypothetical protein OrfI (3587 to 1 to 517). GC content of pTB6 Seas 65.1 mol % and had a level usually observed in the genomic DNA and plasmid DNA of *Bifidobacterium longum*.

The complete nucleotide sequence of pTB6 exhibited 95% homology to *Bifidobacterium longum* plasmids pKJ36 (3625 bp) and pB44 (3624 bp) belonging to the rolling circle replication-type (RCR) plasmid family group 1, 92% homology to pNAC2 (3684 bp), and 89% homology to pBLO1 (3626 bp). Homology as high as 92% was also detected to a plasmid pDOJH10L (5308 to 8999 in 10073 bp) of the group 1 (Table 2).

TABLE 2

Nucleotide homology and aa identity

| | nuc homology | aa identity (%) | | | |
|---|---|---|---|---|---|
| Plasmid | (%)* | RepB** | MobA | MembB | Orf I*** |
| pKJ36 | 95 | 92 | 85 | 88 | — |
| pB44 | 95 | 91 | 85 | — | 31 |
| pNAC2 | 92 | 89 | 58 | — | 31 |

TABLE 2-continued

Nucleotide homology and aa identity

| Plasmid | nuc homology (%)* | aa identity (%) | | | |
|---|---|---|---|---|---|
| | | RepB** | MobA | MembB | Orf I*** |
| pDOJH10L | 92 | 90 | 46 | 57 | 30 |
| pBLO1 | 89 | 81 | 57 | — | 31 |

Numeral shows percent of nuc homology and aa identity to pTB6.
*Complete nuc sequences were compared to that of pTB6 (3,624 bp) except pDOJH10L where nuc position 5308 to 8999 was compared to complete nuc sequence of pTB6.
**Amino acid sequence of RepB from aa position 1 to 230 (pKJ36), from 54 to 283 (pB44), and from 54 to 281 (pNAC2, pDOJH10L and pBLO1) was compared with the complete RepB aa sequence (230 aa) of pTB6. Number of aa in complete RepB was 230, 299, 297, 297, 297 for pKJ36, pB44, pNAC2, pDOJH10L and pBLO1, respectively.
***Orf of pB44, Orf III of pNAC2, Orf II of pDOJH10L, and Orf I of pBLO1 were compared with Orf I.
—Orf homologous to Orf I have not been reported. The GenBank accession numbers for plasmid DNA sequences and plasmid nuc size are AF139129 for pKJ36 (3,625 bp), AY066026 for pB44 (3,624 bp), AY112723 for pNAC2 (3,684 bp), AF538868 for pDOJH10L (10,073 bp) and AF540971 for pBLO1 (3,626 bp).

2. RepB and oriV

The amino acid identity of predicted Orf of pTB6 is shown in Table 2. RepB (230 amino acids (aa)) exhibited 92%, 91%, 90%, 89%, and 81% identity with the complete RepB amino acid sequence (230 aa) of pKJ36, the Rep B as region of amino acids 54 to 283 of pB44, and the RepB as region of amino acids 54 to 281 of pDOJH10L, pNAC2, and pBLO1, respectively. Two local sites, region 1 (aa 117 to 138) and region 2 (aa 183 to 188), were not conserved in these plasmids (FIG. 2(a)).

The replication origin oriV consists of dso (double strand origin) and sso (single strand origin) and is necessary for the initiation of replication of reading and lagging strands (Del Solar et al., Microbiol. Mol. Biol. Rev., 62, 434-494 (1998)). This replication origin was predicted in a region between nucleotides 305 and 664 of pTB6 (FIG. 1(b)). Two sets of IR (305 to 417) were detected in sso, while IR (481 to 504) and DR (577 to 644) were detected in dso (FIG. 1(b)). DR consisted of four identical 22-mer sequences (5'-AACCTACAC-CAAAAGGGGAGCG-3'; SEQ ID NO: 9) except that the last one sequence had T at the 3' terminus. Their 11 nucleotides (5'-CAAAA-3' and 5'-GGAGCG-3') were conserved in the DR of pKJ36 pB44, pNAC2, pDOJH10L, and pBLO1 (FIG. 2(b)). The nucleotide sequence of IR in dso was also conserved in these plasmids except for 2 nucleotides in the loop region (22 of 24 nucleotides) (FIG. 2(c)).

3. MobA and oriT

MobA is a primary DNA processing protein for the conjugative mobilization of the plasmid (Becker et al., J. Bacteriol., 185, 3538-3546 (2003)). The amino acid identity of putative MobA of pTB6 was 85%, 85%, 58%, 57%, and 46% to putative MobA of pKJ36, pB44, pNAC2, pBLO1, and pDOJH10L, respectively (Table 2). MobA of pTB6 also exhibited remarkable similarity to MobA of a plasmid RSF1010 of MOBΩ family (Francia et al., FEMS Microbiol. Rev., 28, 79-100 (2004)). The tyrosine residue of motif I (Francia et al., FEMS Microbiol. Rev., 28, 79-100 (2004)) involved in DNA nicking-closing action and the 3H motif of motif III helping the initiation of transfer by motif I are conserved in MobA of pTB6 (FIG. 3(a)). In oriT of RSF1010, the 13-mer nucleotide sequence 5'-GTAAGTGCGCCCT-3' (SEQ ID NO: 10) adjacent to the inverted repeat is cleaved by MobA (FIG. 3(b)). The region of nucleotides 3454 to 3510 in oriT of pTB6 exhibited structural similarity to the nucleotide sequence seen in oriT of RSF1010 (Francia et al., FEMS Microbiol. Rev., 28, 79-100 (2004)). From these results, the oriT of pTB6 was estimated to be cleaved at the nic site of the 13-mer sequence by MobA expressed from pTB6.

4. MembB and Orf1

MembB of pKJ36 and pDOJH10L exhibited 88% and 57% as identity, respectively, to putative MembB of pTB6. Putative Orf1 of pTB6 consists of 184 as and exhibited considerably low as identity (33% to 31%) to Orf of pB44, OrfIII of pNAC2, OrfII of pDOJH10L, and Orf1 of pBLO1 (Table 2). The functions of these proteins remain unexplained.

5. Essential region to plasmid replication

For understanding the control of plasmid replication, it is important to know the DNA region essential to plasmid replication. The present inventors constructed recombinant plasmids consisting of pUC18, the oriV-repB region (nucleotides 1 to 1872) of pTB6, and spc (1.1 kbp) of pBLES100 (Table 3, FIG. 4). The resulting plasmids pBRASTA100 and pBRASTA101 were extracted from *Escherichia coli* HMS174 and transferred to *Bifidobacterium longum* 105-A. As shown in Table 3, both of the plasmids efficiently transformed *Bifidobacterium longum*. The plasmid pBRSTA100 was transformed to *Bifidobacterium longum* 105-A efficiently ($5.9 \times 10^4$ transformants/μg DNA). This efficiency was as high as that obtained by pBLES100 ($2.2 \times 10^4$ transformants/μg DNA) previously reported. Transformation efficiency 40 times better than that of pBRASTA100 was observed in pBRASTA101 ($2.5 \times 10^6$ transformants/μg DNA). These plasmids were stable in the transformants in terms of the structure and the segregation of phenotypes. An sso-deleted plasmid pDSO44Sp (Table 3, FIG. 4) consisting of pUC18, pTB6 dso-repB, and spc transformed *Bifidobacterium longum* at an efficiency of $1.3 \times 10^6$ transformants/μg DNA (Table 3). On the other hand, the recombinant plasmid pSSO30Sp bearing mobA and a portion of membB (1873 b to 3624 b) but not bearing orf1, oriV, and repB could not transform *Bifidobacterium longum* at all (Table 3). These results concluded that only the presence of the dso-repB region is sufficient for the replication of pTB6 in *Bifidobacterium longum*, and the sso region is not essential.

TABLE 3

Transformation of *B. longum* with plasmid

| Plasmid | Transformants obtained/μg DNA | Ratio |
|---|---|---|
| pBRASTA100 | $5.9 \times 10^4$ | 1.0 |
| pBRASTA101 | $2.5 \times 10^6$ | 42.3 |
| pDSO44Sp | $1.3 \times 10^6$ | 22.0 |
| pSSO30Sp | N.D. | — |
| pBRASTA102 | $7.5 \times 10^4$ | 1.3 |
| pBRASTA103 | $7.3 \times 10^2$ | 0.012 |

Plasmids were prepared from *E. coli* HMS174, and transferred in *B. longum* 105-A. Transformants were selected on agar plate in the presence of Sp. N.D.; Transformants were not detected.

6. High-Efficiency Transformation of *Bifidobacterium longum*

As described above, the plasmid pBRASTA101 was shown to transform *Bifidobacterium longum* at high efficiency exceeding 40 times higher than that of pBRASTA100 and 100 times higher than that of pBLES100. pBRASTA100 and pBLES100 retained a normal amp site, and pBRASTA101 had mutation with half of amp proximal to the promoter deleted (deletion of 0.6 kbp-SspI-FspI DNA segment). For confirming that the deletion in amp actually influences transformation, the 0.6-kbp fragment was inserted into the BamHI site of pBRASTA101, and the obtained pBRASTA102 (FIG. 4) was in turn extracted from *Escherichia coli* HMS174 and transferred into *Bifidobacterium longum* 105-A. As shown in Table 3, almost the same transformation efficiency as that of pBRASTA100 was obtained in pBRASTA102 ($7.5 \times 10^4$ transformants/μg DNA). pBRASTA103 was constructed by inserting the 0.6-kbp fragment into the HindIII site of pBRASTA102. It was shown that this plasmid had 2 copies of this fragment (FIG. 4), and transformation ability was further decreased in proportion to the copy number of the fragment. When these plasmids were transferred to *Escherichia coli* HMS174, such decrease in transformation efficiency was not seen. The accurate mechanism underlying the restriction of the plasmid induced by the 0.6 kbp-DNA remains unexplained. However, these results suggested that plasmid replication is restricted by the cleavage of the 0.6 kbp-DNA transfected into *Bifidobacterium longum* 105-A.

[Discussion]

In the present invention, the nucleotide sequence of the plasmid pTB6 of *Bifidobacterium longum* was determined, and the as sequence of putative Orf was predicted. The results of sequence analysis revealed that pTB6 is a plasmid associated with the RCR plasmid family group 1 reported by Corneau et al (Plasmid, 51, 87-100 (2004)). The high as identity and the high homology of oriV nucleotide sequences between plasmids of the group 1, particularly pKJ36 and pTB6, clearly suggested that pTB6 replicates by the rolling circle mechanism.

The nucleotide sequence conserved in oriT of the MOBΩ-line plasmid was identified in putative oriT of pTB6. Moreover, the remarkable similarity of motif I and motif III of putative MobA to motif I and motif III of the MOBΩ-line plasmid was found in pTB6. This result suggested that pTB6 is mobilized when the factor is further supplied from host cells or other plasmids. From this point of view, the present inventors assume that the plasmids pBRASTA101 and pDSO44Sp having membB and orfI as well as oriT and mobA deleted are useful as safe vehicles of gene transfer.

Recently, Nakamura et al. and Fujimori et al. succeeded in the expression of the cytosine deaminase gene (codA) of *Escherichia coli* in *Bifidobacterium longum* by using the composite plasmid pBLES100 between pBR322 and pTB6. This showed that pTB6 is an useful vector for the expression of a foreign gene in *Bifidobacterium longum*. However, *Bifidobacterium* microorganisms are known to generate site-specific endonuclease. Thus, unmodified DNA may be damaged when introduced into the cells of *Bifidobacterium* microorganisms, (Khosaka et al., Gene. 17, 117-122 (1982); Khosaka et al., FRBS Lett., 14, 63, 170-174 (1983); Khosaka et al., Gene 31, 251-255 (1984); and Skrypina et al., Mol. Gen. Mikrobiol. Virusol., 5, 15-16 (1988)). Because the small plasmids pBRASTA101 and pDSO44Sp lack oriT and mobA and have high transformation ability, the present inventors assume that these plasmids are practical for the cloning and expression of a foreign gene in *Bifidobacterium longum*.

EXAMPLE 2

Construction of Shuttle Vector pAV001

[Construction of Plasmid]

*Enterococcus faecalis*-derived sequence containing spectinomycin adenyltransferase (AAD cassette) was amplified from pBLES100 by PCR and subcloned into pCR-Blunt II-TOPO vector (Invitrogen) to prepare pCRTOPO-ScaI-AAD-Eam1105I. Restriction enzymes sites ScaI and Eam1105I were added to forward and reverse primers, respectively.

As shown in FIG. 5, a cloning vector pGFPuv (DEFINITION: Cloning vector pGFPuv. ACCESSION: U62636 VERSION: U62636.1 GI: 1490528) purchased from Invitrogen is composed of a GFPuv gene, multi-cloning sites (MCS) located at both ends thereof, an ampicillin resistance gene, and a plasmid replication origin Ori (pUC Ori) of *Escherichia coli*.

The ampicillin resistance gene site was cleaved with restriction enzymes Eam1105I and ScaI to prepare a long fragment without the site. Similarly, pCRTOPO-ScaI-AAD-Eam1105I was cleaved with restriction enzymes Eam1105I and ScaI to prepare a fragment (approximately 1100 bp) containing the AAD cassette. These two fragments were ligated by use of T4DNA ligase to prepare pGFPuv-SpR. The addition of a spectinomycin resistance property to the prepared plasmid pGFPuv-SpR and the deficiency of an ampicillin resistance property of the plasmid were respectively confirmed in *Escherichia coli*.

pGFPuv-SpR was digested with restriction enzymes SalI (present in the multi-cloning site upstream of the GFPuv gene) and SpeI (present in the multi-cloning site downstream of the GFPuv gene) to prepare a plasmid pAVN in which the GFPuv gene was deleted.

A sequence of approximately 1900 by containing RepB, SDO, DDO, AT-rich repeats, and DnaA-binding motifs was identified as a plasmid replication unit of *Bifidobacterium longum* from the information on the complete nucleotide sequence of the *Bifidobacterium longum*-derived plasmid pTB6 obtained in Example 1.

The sequence of approximately 1900 by containing the plasmid replication unit of *Bifidobacterium longum* was amplified from pTB6 by PCR and subcloned into pCR-Blunt II-TOPO vector to prepare pCRTOPO-ApaI-1900-ScaI. Restriction enzyme sites ApaI and ScaI were added to forward and reverse primers, respectively.

A long fragment (approximately 2400 bp) obtained from pAVN digested with restriction enzymes ApaI and ScaI and a short fragment (approximately 1900 bp) obtained from pCR-TOPO-ApaI-1900-ScaI digested with restriction enzymes ApaI and ScaI were ligated by use of T4 DNA ligase to prepare a *Bifidobacterium longum-Escherichia coli* shuttle vector pAV001 (approximately 4300 bp).

EXAMPLE 3

Cytosine Deaminase Gene Expression Vector pAV001-HU-eCD

[Construction of Expression Vector]

Next, pBLES100-S-eCD was cleaved with restriction enzymes HindIII and SpeI to extract a sequence of approximately 2900 by containing a HU gene promoter, an *Escherichia coli*-derived cytosine deaminase gene, and a HU gene terminator. A long fragment obtained from the shuttle vector pAV001 cleaved at the restriction enzyme sites in the multi-cloning site with HindIII and SpeI and the above fragment of approximately 2900 bp were ligated by use of T4 DNA ligase to prepare pAV001-HU-eCD (approximately 7100 bp).

[Comparison of Plasmid Copy Number in *Bifidobacterium longum*]

The pAV001-HU-eCD and pBLES100-S-eCD constructed this time were respectively introduced into *Bifidobacterium longum* to prepare two recombinant microorganisms, *Bifidobacterium longum*:: pAV001-HU-eCD and *Bifidobacterium longum*::pBLES100-S-eCD. The presence of the respective plasmids was confirmed by PCR. *Bifidobacterium longum*:: pAV001-HU-eCD and *Bifidobacterium longum*::pBLES100-S-eCD were respectively subcultured at 37° C. for 2 or more days in MRS media (OXID) under anaerobic conditions. The respective bacterial cells ($1 \times 10^9$ CFU) were separated by centrifugation from the resulting culture media, and total DNAs were extracted by using Puregene DNA Isolation Kit (Gentra Systems). The collected total DNAs were digested with restriction enzymes HindIII and Eco81I, and nucleic acids were separated by agarose gel electrophoresis and subjected to Southern analysis using AlkPhos Direct Labelling Reagents (Amersham Bioscience) to compare plasmid copy numbers (see FIG. 9A). For a sensitization method of signals, the nucleic acids allowed to develop chemiluminescence with alkaline phosphatase were exposed to X-ray films. In the comparison of signal intensity, the X-ray films after exposure were scanned using a gel scanning system (ATTO), and the obtained scan images were analyzed with CS analyzer (software; ATTO) to determine plasmid copy numbers. As a result, the plasmid copy number of pBLES100-S-eCD was approximately 3.26/cell, whereas the plasmid copy number of pAV001-HU-eCD was approximately 11.68/cell. Therefore, the plasmid copy number of pAV001-HU-eCD was confirmed to be 3.6 times larger than that of pBLES100-S-eCD, and significant difference was observed in the number of the pAV001-HU-eCD plasmid replicating, when compared to that of pBLES100-S-eCD (see FIG. 9B).

[Comparison of Expression Level of Cytosine Deaminase Protein in *Bifidobacterium longum*]

*Bifidobacterium longum*::pAV001-HU-eCD and *Bifidobacterium longum*::pBLES100-S-eCD were respectively subcultured at 37° C. for 2 or more days in MRS media under anaerobic conditions. The respective bacterial cells ($1\times10^9$ CFU) were separated by centrifugation from the resulting culture media and disrupted by ultrasonication to extract the respective proteins in the bacterial cells. The above extracted proteins were separated by SDS-polyacrylamide gel electrophoresis, and the signal intensity of cytosine deaminase proteins was compared by Western analysis. A rabbit anti-cytosine deaminase monoclonal antibody (Sawaday Technology) and a horseradish peroxidase-conjugated anti-rabbit immunoglobulin G complex (Santa Cruz Biotechnology, Inc) were used as primary and secondary antibodies, respectively. For a sensitization method of signals, the proteins allowed to develop light by an ECL method were exposed to X-ray films. In the comparison of signal intensity, the X-ray films after the exposure were scanned using a gel scanning system (ATTO), and the obtained scan images were analyzed with CS analyzer (software; ATTO) to compare the expression levels. The result is shown in FIG. 6. The result of comparison of signal intensity revealed that *Bifidobacterium longum*::pAV001-HU-eCD expresses the cytosine deaminase protein 2 to 8 times compared to *Bifidobacterium longum*: pBLES100-S-eCD

[Comparison of Enzyme Activity of Cytosine Deaminase Protein (Comparison of Activity of Converting 5FC to 5FU) in *Bifidobacterium longum*]

In addition to *Bifidobacterium longum*::pAV001-HU-eCD (D) and *Bifidobacterium longum*::pBLES100-S-eCD (B), a wild-type strain of *Bifidobacterium longum* (A) and *Bifidobacterium longum*::pAVN without the introduced cytosine deaminase gene (C) used as controls were respectively subcultured at 37° C. for 2 or more days in MRS media under anaerobic conditions. The respective bacterial cells ($2\times10^9$ CFU) were separated by centrifugation from the resulting culture media and resuspended in 4.5 ml of MRS media. Subsequently, the cells were supplemented with 0.5 ml of 5FC (20 mg/ml) at the final concentration of 2 mg/ml and cultured at 37° C. under anaerobic conditions. The respective supernatants from which the bacterial cells were removed by centrifugation were collected from the culture media on 0, 4, 8, 18 and 24 hours to measure a converted 5FU concentration by gas chromatography (5FU GC-MS methods, BML). A temporal shift in bacterial counts is shown in FIG. 7, and the 5-FU concentration is shown in FIG. 8. The results of analysis revealed that the amount of 5FU converted in *Bifidobacterium longum*::pAV001-HU-eCD (D) was approximately 1.83 times (on 4 hours), approximately 1.52 times (on 8 hours), approximately 1.34 times (on 18 hours), approximately 1.57 times (on 24 hours), and approximately 1.57 times (on average) larger than those in *Bifidobacterium longum*:: pBLES100-S-eCD (B).

(Gene Transfer of Cytosine Deaminase Gene Expression Vector pAV001-HU-eCD to Microorganisms of Genus *Bifidobacterium*)

The cytosine deaminase gene expression vector pAV001-HU-eCD was introduced into bacterial strains by electroporation shown in Table 4 to prepare recombinant strains of *Bifidobacterium*.

TABLE 4

| | Bacterial strains |
|---|---|
| 1 | *Bifidobacterium longum* (standard strain of common name: *Bifidobacterium infantis*) JCM1222 |
| 2 | *Bifidobacterium longum* (standard strain of common name: *Bifidobacterium lactenis*) JCM1210 |
| 3 | *Bifidobacterium breve* (standard strain) JCM1190 |
| 4 | *Bifidobacterium longum* aE-194b strain |
| 5 | *Bifidobacterium longum* bs-601 strain |

At present, infantis and lactenis are included as subspecies of longum in longum from the standpoint of taxonomy while as they were previously known as distinct bacterial species belonging to the genus *Bifidobacterium*.

(Measurement of Cytosine Deaminase Activity of Recombinant Strains of *Bifidobacterium*)

After the culture of the recombinant strains of *Bifidobacterium*, the respective bacterial cells were centrifuged from the resulting culture media, then suspended in buffer solutions containing 50 mM HEPES, and disrupted in a ultrasonicator. These disruption solutions were centrifuged, and the supernatants from which unnecessary fractions were removed were used as extracted protein samples. Aliquots corresponding to the total protein amount of 0.05 mg were taken from the extracted protein samples and supplemented with a buffer solution to exactly adjust the total amount to 250 µL. Further, 250 µL of 20 mM 5FS solution was exactly added to the resulting solutions, which were then incubated at 37° C. for 60 minutes in water bath. After the addition of trichloroacetic acid thereto and extraction, the samples neutralized with sodium hydroxide were measured by HPLC for the amount of 5FU produced and the amount of 5FC remaining. HPLC measurement was conducted twice to confirm that there were only a few measurement error.

The cytosine deaminase gene expression vector pAV001-HU-eCD using the novel shuttle vector pAV001 was capable to introduce five bacterial strains shown in Table 4. Moreover, the transgene cytosine deaminase was actually highly expressed as a protein having activity, and the activity was high (see Table 5).

TABLE 5

| Sample | 5FU (mM) | average 5FU | 5FC (mM) | Amount of 5FC converted (%) |
|---|---|---|---|---|
| *Bifidobacterium infantis*/ pAV001-HU-eCD | 1.767 1.768 | 1.767 | 8.024 8.119 | 18.0 |
| *Bifidobacterium lactenis*/ | 0.999 | 1.006 | 9.148 | 9.8 |

TABLE 5-continued

| Sample | 5FU (mM) | average 5FU | 5FC (mM) | Amount of 5FC converted (%) |
|---|---|---|---|---|
| pAV001-HU-eCD | 1.013 | | 9.293 | |
| Bifidobacterium breve/ pAV001-HU-eCD | 0.848 0.840 | 0.844 | 9.029 8.967 | 8.6 |
| Bifidobacterium longum aE-194b strain/ pAV001-HU-eCD | 0.595 0.597 | 0.596 | 9.233 9.230 | 6.1 |
| Bifidobacterium longum bs-601 strain/ pAV001-HU-eCD | 0.637 | 0.637 | 9.543 | 6.3 |

INDUSTRIAL APPLICABILITY

According to the present invention, a shuttle vector for a microorganism of the genus Bifidobacterium and Escherichia coli having a wide host range and a large copy number in microorganisms of the genus Bifidobacterium and capable of highly expressing of a desired protein in a microorganism of the genus Bifidobacterium when used as an expression vector; an expression vector capable of expressing a desired gene in a microorganism of the genus Bifidobacterium by use of the shuttle vector; a microorganism of the genus Bifidobacterium transformed with the expression vector; and an antitumor agent comprising the microorganism of the genus Bifidobacterium as an active ingredient can be obtained.

The invention claimed is:

1. A pTB6-derived replication unit of a microorganism of the genus *Bifidobacterium* comprising the dso of the replication origin (oriV) and the repB region of pTB6 but not comprising the MembB, MobA, OrfI and oriT regions of pTB6.

2. The pTB6-derived plasmid replication unit of the microorganism of the genus *Bifidobacterium* according to claim 1, wherein the pTB6-derived plasmid replication unit is nucleotides 305 to 1564 in SEQ ID NO:1.

3. The pTB6-derived plasmid replication unit of the microorganism of the genus *Bifidobacterium* according to claim 1, wherein the plasmid replication unit does not comprise an ampicillin resistance gene.

4. A shuttle vector for a microorganism of the genus *Bifidobacterium* and *Escherichia coli* comprising a pTB6-derived region portion and an *Escherichia coli*-derived plasmid portion, wherein (a) the pTB6-derived region portion comprises the double strand origin (dso) of the replication origin (oriV) and the repB region of pTB6, but does not comprise the MembB, MobA, OrfI, and oriT regions of pTB6, and (b) the *Escherichia coli*-derived plasmid portion comprises pUC ori.

5. The shuttle vector for a microorganism of the genus *Bifidobacterium* and *Escherichia coli* according to claim 4, wherein the pTB6-derived region portion is nucleotides 305 to 1564 in SEQ ID NO:1.

6. The shuttle vector according to claim 4, further comprising an expression unit of a desired gene ligated in-frame between a promoter and terminator involved in the expression of a *Bifidobacterium longum*-derived gene encoding a histone-like DNA-binding protein (HU protein), wherein the promoter and terminator consist of nucleotides 1 to 192 and 472 to 600 of SEQ ID NO:2, respectively.

7. The shuttle vector according to claim 6, wherein the desired gene is a gene encoding a cytokine having antitumor activity, a gene encoding an angiogenic inhibitor, or a gene encoding an enzyme capable of converting an antitumor substance precursor into an antitumor substance.

8. The shuttle vector according to claim 7, wherein the gene encoding an enzyme capable of converting an antitumor substance precursor into an antitumor substance is a cytosine deaminase gene.

9. A microorganism of the genus *Bifidobacterium* transformed with the shuttle vector for a microorganism of the genus *Bifidobacterium* and *Escherichia coli* according to any one of claims 4, 5, 6, 7 and 8.

10. The microorganism of the genus *Bifidobacterium* according to claim 9, which is *Bifidobacterium longum*, *Bifidobacterium adolescentis*, *Bifidobacterium bifidum*, *Bifidobacterium pseudolongum*, *Bifidobacterium thermophirum*, *Bifidobacterium breve*, *Bifidobacterium infantis*, or *Bifidobacterium animalis*.

11. A microorganism of the genus *Bifidobacterium* transformed with the shuttle vector according to any one of claim 6, 7, or 8.

12. The microorganism of the genus *Bifidobacterium* according to claim 11, which is *Bifidobacterium longum*, *Bifidobacterium adolescentis*, *Bifidobacterium bifidum*, *Bifidobacterium pseudolongum*, *Bifidobacterium thermophirum*, *Bifidobacterium breve*, *Bifidobacterium infantis*, or *Bifidobacterium animalis*.

13. An antitumor agent comprising the microorganism of the genus *Bifidobacterium* according to claim 11 as an active ingredient.

14. An antitumor agent comprising the microorganism of the genus *Bifidobacterium* according to claim 12 as an active ingredient.

15. The shuttle vector of claim 6, wherein the desired gene is inserted into a site developed using restriction sites downstream of the promoter.

16. The shuttle vector of claim 15, wherein the restriction sites are Nsp V and Hpa I.

* * * * *